(12) United States Patent
Fisher et al.

(10) Patent No.: US 12,201,619 B2
(45) Date of Patent: Jan. 21, 2025

(54) COMPOUNDS AND METHODS FOR USE IN THE TREATMENT OF MICROGLIA-MEDIATED DISORDERS

(71) Applicant: NSC Therapeutics GmbH, St. Radegund/Graz (AT)

(72) Inventors: Abraham Fisher, Holon (IL); Stefan Grathwohl, Unterengstringen (CH); Roger Nitsch, Zumikon (CH)

(73) Assignee: NSC Therapeutics GmbH, St. Radegund/Graz (AT)

( * ) Notice: Subject to any disclaimer, the term of this patent is extended or adjusted under 35 U.S.C. 154(b) by 0 days.

(21) Appl. No.: 16/982,890

(22) PCT Filed: Mar. 22, 2019

(86) PCT No.: PCT/EP2019/057276
§ 371 (c)(1),
(2) Date: Sep. 21, 2020

(87) PCT Pub. No.: WO2019/180224
PCT Pub. Date: Sep. 26, 2019

(65) Prior Publication Data
US 2021/0000807 A1  Jan. 7, 2021

(30) Foreign Application Priority Data
Mar. 22, 2018 (EP) ..................................... 18163461

(51) Int. Cl.
A61K 31/439 (2006.01)
A61K 31/438 (2006.01)

(52) U.S. Cl.
CPC .......... *A61K 31/439* (2013.01); *A61K 31/438* (2013.01)

(58) Field of Classification Search
CPC ............................. A61K 31/438; C07D 417/04
See application file for complete search history.

(56) References Cited

U.S. PATENT DOCUMENTS

| | | | | |
|---|---|---|---|---|
| 7,049,231 | B2 * | 5/2006 | Nuttall | C23C 16/04 438/674 |
| 7,439,251 | B2 * | 10/2008 | Fisher | A61P 1/00 514/278 |
| 11,008,342 | B2 * | 5/2021 | Fisher | A61P 27/02 |
| 2020/0040007 | A1 | 2/2020 | Fisher et al. | |
| 2021/0000807 | A1 * | 1/2021 | Fisher | A61K 31/438 |

FOREIGN PATENT DOCUMENTS

| | | | | |
|---|---|---|---|---|
| EP | 0205247 | A2 | 12/1986 | |
| WO | WO-9503303 | A2 * | 2/1995 | .............. A61P 25/16 |
| WO | WO-03/092580 | A2 | 11/2003 | |
| WO | WO-2018/065529 | A1 | 4/2018 | |

OTHER PUBLICATIONS

Fassihi, R. (2017) "Modified-Release Delivery Systems: Extended-Release Capsule Platform." In Eds. Augsburger, L. L. and Hoag, S. W., Pharmaceutical Dosage Forms: Capsules (pp. 317-344). CRC Press. (Year: 2017).*
Zhong et al. "Soluble TREM2 induces inflammatory responses and enhances microglial survival" J. Exp. Med. 2017, 214, 597-607. (Year: 2017).*
U.S. Dept. of Health and Human Services et al. (Jan. 29, 2018). Early Alzheimer's Disease: Developing Drugs for Treatment. Guidance for Industry. Revision 1. (Year: 2018).*
Ashizawa, "Physico-chemical studies on the molecular details of drug crystals," Pharm Tech Japan. 18(10):81-96, 210 (1629-1644, 1758) (2002) (18 pages).
Office Action dated Feb. 16, 2021 for Japanese Patent Application No. 2019-512714, Fisher et al., "Crystalline Polymorphs of a Muscarinic Acetylcholine Receptor Agonist," filed Oct. 5, 2017 (8 pages).
Ooshima et al., "Crystallization of polymorphs and pseudo-polymorphs and its control," Pharm Stage. 6(10):48-53 (2007) (9 pages).
Takata et al., "API form screening and selection in drug discovery stage," Pharm Stage. 6(10):20- 25 (2007) (9 pages).
Brittain, "Spectral methods for the characterization of polymorphs and solvates," J. Pharm. Sci. 86(4):405-412 (1997).
Byrn et al., "Pharmaceutical solids: a strategic approach to regulatory considerations," Pharm. Res. 12(7):945-954 (1995).
Decision of the Boards of Appeal of the European Patent Office for Case No. T 0777/08 dated May 24, 2011, retrieved from <http://www.epo.org/law-practice/case-law-appeals/pdf/t080777ex1.pdf> (17 pages).
International Search Report and Written Opinion mailed Nov. 24, 2017, for PCT International Patent Application No. PCT/EP2017/075373, Fisher et al., "Crystalline Polymorphs of a Muscarinic Acetylcholine Receptor Agonist," filed Oct. 5, 2017 (13 pages).
Beach et al., "Reduction of cerebrospinal fluid amyloid beta after systemic administration of M1 muscarinic agonists," Brain Res. 905(1-2):220-223 (2001).
Fisher et al., "M1 agonists for the treatment of Alzheimer's disease. Novel properties and clinical update," Ann. N.Y. Acad. Sci. 777:189-196 (1996).

(Continued)

*Primary Examiner* — Amanda L. Aguirre
(74) *Attorney, Agent, or Firm* — Jones Day

(57) ABSTRACT

Provided are M1 muscarinic acetylcholine receptor (mAChR) agonists, for use in the treatment of a neurological or neurodegenerative disease by promoting microglia and/or macrophage viability and/or activation. Microglia and macrophage survival and activation are thereby achieved by increasing levels of sTREM2 released by microglia cells. In addition, pharmaceutical compositions and methods of preparing the same are described, which are suitable for the treatment or prevention of conditions or diseases that require microglia and/or macrophage modulation, as well as methods for monitoring treatments and enhancing microglia and/or macrophage survival and/or activation.

15 Claims, 8 Drawing Sheets

(56) References Cited

OTHER PUBLICATIONS

International Search Report and Written Opinion mailed Jun. 5, 2019 for PCT International Application No. PCT/EP2019/057276, Fisher et al., "Compounds and Methods for Use in the Treatment of Microglia-Mediated Disorders," filed Mar. 22, 2019 (11 pages).

Bellou et al., 2017, "Systematic evaluation of the associations between environmental risk factors and dementia: An umbrella review of systematic reviews and meta-analyses," Alzheimer's & Dementia, 13:406-418.

Hersi et al., 2017, "Risk factors associated with the onset and progression of Alzheimer's disease: A systematic review of the evidence," NeuroToxicology, 61:143-187.

Jay et al., 2017, "TREM2 in Neurodegenerative Diseases," Molecular Neurodegeneration, 12:56.

Kanatsu and Tomita, 2017, "Molecular mechanisms of the genetic risk factors in pathogenesis of Alzheimer Disease," Frontiers in Bioscience, Landmark, 22:180-192.

Karch and Goate, 2015, "Alzheimer's Disease Risk Genes and Mechanisms of Disease Pathogenesis," Biological Psychiatry, 77:43-51.

Larsson et al., 2017, "Modifiable pathways in Alzheimer's disease: Mendelian randomization analysis," BMJ, 359:j5375.

Reitz and Mayeux, 2014, "Alzheimer disease: Epidemiology, diagnostic criteria, risk factors and biomarkers," Biochemical Pharmacology, 88:640-651.

Yeh et al., 2017, "TREM2, Microglia, and Neurodegenerative Diseases," Trends in Molecular Medicine, 23(6):512-533.

\* cited by examiner tTREM2 level analysis in primary microglia

COMPOUNDS AND METHODS FOR USE IN THE TREATMENT OF MICROGLIA-MEDIATED DISORDERS

FIELD OF THE INVENTION

The present invention relates to small molecules, preferably non-proteinaceous compounds that as M1 muscarinic acetylcholine receptor (mAChR) agonists are used for the treatment of microglia-mediated neurological and neurodegenerative diseases by promoting microglia survival and activation, pharmaceutical compositions and methods of treatment.

BACKGROUND OF THE INVENTION

Neurological or neurodegenerative diseases as well as infections of the central nervous system can trigger local inflammation and consequently activation of an immune response. Specifically, Alzheimer's disease (AD) is characterized by an inflammatory response to amyloid-β, inducing the activation of microglia which constitute a first line of defense against invading pathogens or other types of brain tissue injury and are understood to be the "sentinels" of the central nervous system. Under pathological conditions, such as neurodegenerative disease, stroke, and tumor invasion, microglia become activated, surround damaged and dead cells, and clear cellular debris. Microglia react to injury and degeneration with immune-phenotypic and morphological changes, proliferation, migration, and inflammatory cytokine production (Shaftel et al., J. Clin. Invest. 117 (2007), 1595-1604). Although it remains controversial whether their role in disease progression is protective or harmful overall, it is commonly acknowledged that microglia play a major role in neurological and neurodegenerative diseases; see Prokop et al., Acta Neuropathol 126 (2013), 461-77 for review. Accordingly, targeting microglia provides an interesting new avenue in the development of novel treatments for these diseases. Current approaches mostly aim at reducing microglia activation and production of pro-inflammatory cytokines in order to avoid neuroinflammation-mediated neuronal damage (reviewed, e.g., in Solito and Sastre, Front Pharmacol 3 (2012), 14 and Wang et al., Ann. Transl. Med. 3 (2015): 136).

Genetic variations in the triggering receptor expressed on myeloid cells 2 (TREM2) reported to disturb proper microglia function (loss-of-function variants) are linked to a spectrum of neurodegenerative disorders including AD, frontotemporal dementia (FTD), Parkinson's disease (PD), amyotrophic lateral sclerosis (ALS) and Nasu-Hakola disease (NHD, also known as polycystic lipomembranous osteodysplasia with sclerosing leukoencephalopathy, PLOSL) (reviewed in Yeh et al., Trends Mol. Med. 23 (2017), 512-533). TREM2 is expressed by microglia and promotes microglia survival, activation, and the formation of a protective microglia barrier around amyloid plaque. Studies have shown that TREM2-mediated activities are intimately involved in neurodegenerative diseases and therefore provide a new therapeutic target. Specifically, the in vitro and in vivo treatment of microglia and mouse hippocampi with transgenic soluble TREM2 (sTREM2) protein revealed a protective effect on microglial viability and a trigger of microglial activation (Zhong et al., J. Exp. Med. 214 (2017), 597-607). However, the application of genetically engineered protein-based drugs is highly inconvenient, cumbersome and expensive as well as at risk of eliciting an undesired immunogenic response to the protein therapeutic and inadequate exposure due to poor blood-brain-barrier passage.

Accordingly, there is still a need for drugs that promote microglia survival and activation for a safe and tolerable treatment of neurological and neurodegenerative diseases.

This problem is solved by the present invention in accordance with the embodiments as characterized in the claims and described further below.

SUMMARY OF THE PRESENT INVENTION

The present invention generally relates to compounds for triggering the release of the soluble form of receptor expressed on myeloid cells 2 (sTREM2). More specifically, the present invention relates to the use of such compounds, which are preferably agonists of the human M1 muscarinic acetylcholine receptor (mAChR) in the treatment of neurological and neurodegenerative disorders in a subject by promoting microglia and/or macrophage cellular viability and/or activation. In accordance with the present invention the M1 mAChR agonist is preferably selected from a compound having the formula (I):

wherein:

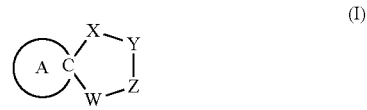

(I)

C denotes a spiro carbon atom shared by ring A and the ring containing X, Y, Z and W;

A is selected from the group consisting of:

wherein R is selected from H, $C_{1-6}$-alkyl, and optionally substituted $C_{1-6}$-alkyl;

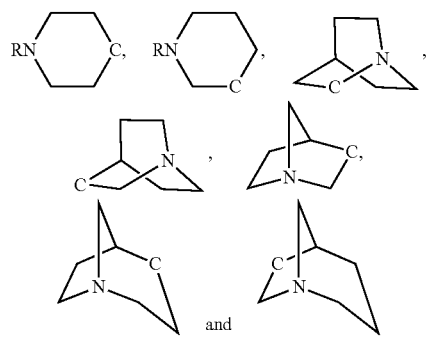

and

X is —O—, —S—, or —NH—;
Y is —$CR^1R^2$— or —$C(R^1)$=;
Z is selected from the group consisting of —O—, —S—, =N—, —C(=O)—, or —C(=S)—;
W is selected from the group consisting of —$CH_2$—, or —NH—;
R, $R^1$, $R^2$ are each independently selected from H, $C_1$-$C_8$ straight- or branched-chain alkyl, or an enantiomer, diastereomer, racemate, tautomer, geometrical isomer, metabolite as crystalline or amorphous forms or pharmaceutically acceptable salt as crystalline or amorphous forms thereof.

The compound for use in accordance with the present invention is preferably characterized by showing an intracellular calcium mobilization response in Chinese Hamster Ovary cells expressing the human M1 mAChR (CHOM1 cells) with respect to carbachol (CCh) of at least 90% (see Example 1). Furthermore, the compound is capable of inducing phosphoinositide (PI) hydrolysis in said CHOM1 cells at 1 mM with a maximal response of at least 50% of the maximal response obtained with 100 µM CCh (see Example 2).

In one embodiment of the present invention the compound has the formula (II)

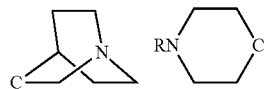
(II)

wherein:
A is selected from the group consisting of:

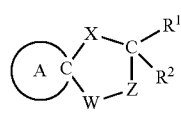

wherein:
R is $CH_3$; $R^1$ is H and $R^2$ is selected from $CH_3$ or $CH_2CH_3$; and
Z is selected from the group consisting of =N—, —O— or —S—, —C(=O)—.

In preferred embodiment of the present invention the compound is (S)-2-ethyl-8-methyl-1-thia-4,8-diaza-spiro[4.5]decan-3-one (NSC001, AF267B) having the formula:

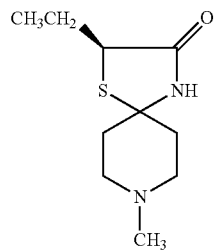

In a particular preferred embodiment, the compound is a crystalline polymorph of NSC001 which is disclosed in PCT/EP2017/075373 (see, e.g., pages 12 to 14, listing of the Forms I to III and their characteristics) and is therefore selected from the group consisting of:

Monohydrate Form I
  (i) having an X-ray powder diffraction pattern containing at least one of the following 2-theta values (±0.2) as measured using $CuK_\alpha$ radiation: 8.8, 12.3, 17.5, 19.9, 21.6, 23.5, 24.5, 26.3, 28.8, and 31.6, but lacks at least one of the following 2-theta values: 17.3, 17.9, 21.9, 24.9, 29.3, 30.8, and 33.4; see also FIG. 1 of PCT/EP2017/075373;
  (ii) wherein the ZnSe ATR-FT-IR absorption spectrum of the crystalline form contains at least one absorption peak having a value selected from 1352, 1369 and 1387 $cm^{-1}$; and/or
  (iii) wherein the crystalline form exhibits an endothermic peak at 107.1° C. (onset at 104.85° C.) and 136.17° C. (onset at 133.41° C.) as measured by differential scanning calorimetry (DSC); and optionally; see also FIG. 3 of PCT/EP2017/075373;
  (iv) wherein the $^{13}C$ solid-state NMR of the crystalline form contains at least one resonance having one of the following chemical shift values as expressed in ppm relative to TMS: 67.09, 54.08, 46.59, 40.97, 30.15 and 13.27; and/or
  (v) wherein the $^{13}C$ solid-state NMR of the crystalline form contains a difference in chemical shift between the resonance having the largest chemical shift and another resonance of 107.3, 120.3, 127.8, 133.4, 144.2 or 161.1, Anhydrous Form II
  (i) that exhibits a single crystal X-ray characterized by the following single crystal X-ray data: P2 (1) a=8.1416 (13), (a=90°, b=7.9811 (12) (β=90.761 (2)°, c=17.878 (3), (γ=90°, Å, T=173 (1) K; see also FIG. 11 of PCT/EP2017/075373;
  (ii) having an X-ray powder diffraction pattern containing at least one of the following 2-theta values (±0.2) as measured using $CuK_\alpha$ radiation: 9.9, 10.8, 11.8, 11.9, 14.8, 16.2, 18.2, 18.5, 19.8, 21.3, 22.4, 23.9, 29.2, 29.7, and 33.1; see also Table 1 of PCT/EP2017/075373;
  (iii) wherein the ZnSe ATR-FT-IR absorption spectrum of the crystalline form contains at least one absorption peak having a value selected from 1906, 1340, 1447, 2869, 2901, 2951, and 3006-3012 $cm^{-1}$;
  (iv) wherein the $^{13}C$ solid-state NMR of the crystalline form contains at least one resonance having one of the following chemical shift values as expressed in ppm relative to TMS: 175.0, 65.3, 64.0, 45.8, 45.0, 49.3, 43.6, 39.5, 38.8, 28.9, 26.0, 15.4, 14.8; see also Table 5 of PCT/EP2017/075373;
  (v) wherein the $^{13}C$ solid-state NMR of the crystalline form contains a difference in chemical shift between the resonance having the largest chemical shift and another resonance of 109.7 or 111; 129.2 or 130.0; 122.7; 125.7; 131.4; 135.5; 136.2; 146.1 or 149.0; and 159.6 or 160.2; and/or
  (vi) wherein the crystalline form has an endothermic peak with an onset at 134.2° C. and peak at 135.4° C.±0.2° C. and substantially no endothermic peak between 106° C. and 110° C., lacking an endotherm peak in the range of about 50° C. to about 120° C., as measured by DSC; see also FIG. 7 of PCT/EP2017/075373, or Monohydrate Form III
  (i) having an X-ray powder diffraction pattern containing at least one of the following 2-theta values (±0.2) as measured using $CuK_\alpha$ radiation: 12.3, 17.3, 17.5, 19.9, 21.6, 24.4, 26.3, and 35.4, and substantially free of peaks having 2-theta values in the range of 10.8-11.9; see also Table 2 of PCT/EP2017/075373;
  (ii) wherein the $^{13}C$ solid-state NMR of the crystalline form contains at least one resonance having one of the following chemical shift values as expressed in ppm relative to TMS: 67.56, 54.60, 47.97, 41.49, 30.70 and 13.77; see also Table 5 of PCT/EP2017/075373;
  (iii) wherein the $^{13}C$ solid-state NMR of the crystalline form contains a difference in chemical shift between the resonance having the largest chemical shift and another resonance of 107.3, 120.3, 127.0, 133.4, 144.2 or 161.1;
  (iv) wherein the ZnSe ATR-FT-IR absorption spectrum of the crystalline form contains at least one absorption peak having a value selected from 1039, 1353, 1369, 1369, 1388, 2918, 2974 and 3088 $cm^{-1}$; and/or (v) wherein the crystalline form exhibits a very broad endothermic peak at 58-94° C. and an endothermic peak with an onset at 133.7° C. and a peak at 134.9° C. as measured by DSC; see also FIG. 4 and Table 3 of PCT/EP2017/075373.

In a most preferred embodiment of the present invention, the compound is crystalline polymorph Form II or Form III of AF267B (NSC001) disclosed in PCT/EP2017/075373.

In another preferred embodiment the compound for use in accordance with the present invention is cis-2-Methylspiro [1,3-oxathiolane-5,3'-quinuclidine] hydrochloride (AF102B, Cevimeline) having the formula:

In one embodiment of the present invention the compound is administered in an amount effective to increase the level of soluble triggering receptor released from myeloid cells 2 (sTREM2) in order to promote cellular viability and/or to activate microglia cells and/or macrophages.

In a further embodiment of the invention, the subject to be treated with the compound is negative for a mutation that impairs the biological activity of sTREM2 and has at least one functional allele of the TREM2 encoding gene, respectively. In another embodiment of the invention, the subject to be treated with the compound is positive for a mutation resulting in a reduced biological activity of sTREM2, for example the amino acid substitution R47H or R62H in the sequence of sTREM2.

In a still further embodiment of the invention, the treatment comprises administering to the subject 1 mg to 100 mg of the compound, preferably 10 mg to 50 mg. In yet further embodiment the compound is administered as oral solution or oral pill.

In one embodiment of the invention, the disease or condition to be treated is selected from the group consisting of brain amyloidoses and TREM2-mediated disorders, i.e. disorders due to reduced availability of sTREM2.

In another aspect, the invention relates to a pharmaceutical composition for use in the treatment of a neurodegenerative or neurological disease comprising the compound and at least one pharmaceutically acceptable excipient or carrier. Thereby, the pharmaceutical composition preferably is a formulation of a crystalline polymorph of the compound, which is suitable for oral administration, and wherein the formulation is (i) directly compressed into tablets; or (ii) mixed with one or more excipient(s) (pregelatinized starch, microcrystalline cellulose, colloidal silicon dioxide, and stearic acid) and the mixture is filled in size 4, white opaque, hard gelatin, two-piece capsules to provide 5 mg or 10 mg of the compound per capsule, which can be used as an oral formulation for immediate release in the gastrointestinal tract.

In a further aspect the present invention relates to a method for the prevention or treatment of a neurological or neurodegenerative disorder comprising administering to a subject in need thereof the compound or the pharmaceutical of the invention in a therapeutically effective amount to increase the level of sTREM2. Furthermore, in one embodiment a method is provided to enhance microglia and/or macrophage survival and/or activation by administering the compound or pharmaceutical composition of the invention to the subject in a therapeutically effective amount.

In yet another aspect the present invention relates to an in vitro method of promoting cellular viability and/or activation of microglia cells and/or macrophages comprising contacting a cell culture comprising microglia cells and/or macrophages with the compound of the invention.

In a further aspect the invention relates to a method of monitoring the efficacy of the treatment of a subject suffering from or disposed to develop a neurodegenerative or inflammatory disease or disorder with a compound for use in accordance with the present invention, comprising
(a) assaying the level of sTREM2 in a sample of the subject's body fluid, preferably cerebrospinal fluid (CSF) at a specified time interval following (preferably peripheral) administration of the compound, wherein the compound can trigger the release of sTREM2 to alter the level of and net efflux of sTREM2 from brain to the body fluid;
(b) comparing the assayed level of sTREM2 in the body fluid sample to a reference standard; wherein the difference or similarity between the level of sTREM2 in the body fluid sample and the reference standard correlates with the level of sTREM2 in the brain of the subject.

Furthermore, the present invention relates to a method of preparing a pharmaceutical composition comprising an M1 mAChR agonist having the effect of enhancing microglial and/or macrophage survival and/or activation; said M1 mAChR agonist having been contacted in vitro with a microglia cell and/or macrophage, and determined to stimulate secretion of sTREM2 from the mammalian microglia cell and/or macrophage, wherein the ability of the M1 mAChR agonist to stimulate sTREM2 secretion from the mammalian microglia cell and/or macrophage is indicative of the agonist being a compound useful for treating or preventing a condition ameliorated by enhancing microglial and/or macrophage survival and/or activation; said method comprising admixing the agonist with a pharmaceutically acceptable carrier.

The embodiments of the present invention will be further described in detail by way of the accompanying Figures and Examples.

DETAILED DESCRIPTION OF THE INVENTION

Figure 1:
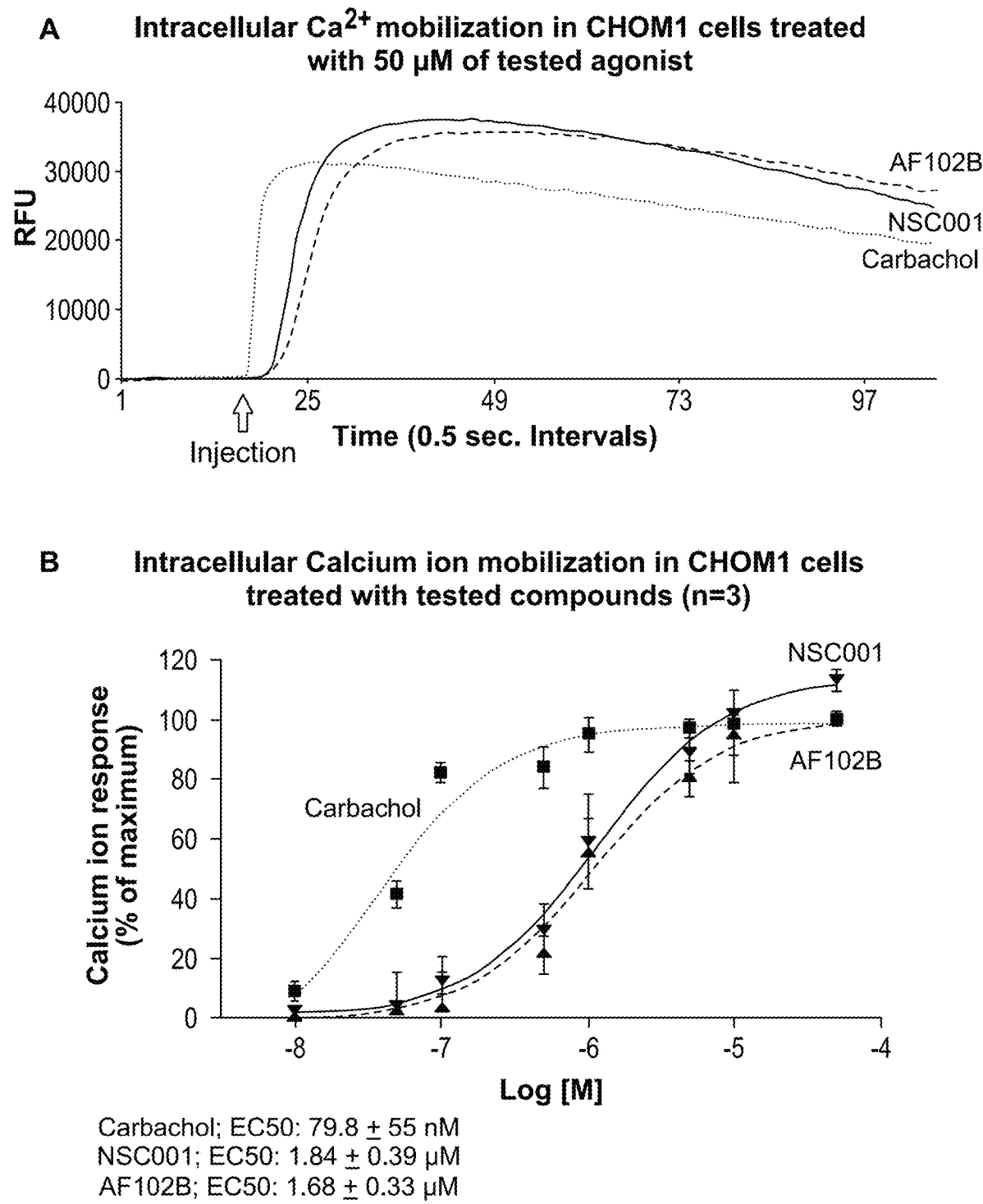
FIG. 1: Intracellular calcium ion mobilization measurement of the compounds NCS001 (AF267B), AF102B and carbachol (CCh) in CHO cells expressing the M1 mAChR (CHOM1) (A). Intracellular calcium ion mobilization in CHOM1 cells treated with 50 μM of NSC001 or AF102B results in a high calcium mobilization response relative to CCh (113% and 101%, respectively) (B). The EC50 values are 79.8±55 nM for CCh, 1.84±0.39 μM for NSC001 and 1.68±0.33 μM for AF102B.

The present invention relates to small molecule compounds that promote microglia and macrophage survival and activation by increasing the release of sTREM2 from microglia and macrophages, which are considered to prove useful in the treatment of various neurodegenerative diseases and that are conveniently administered, preferably inexpensive, well tolerated and safe and advantageously are capable of crossing the blood-brain barrier (BBB). The term "small molecule" typically denotes an organic compounds that cross the BBB and have the dual molecular characteristics of (a) molecular weight under a 400-500 Dalton threshold and (b) lipid solubility; see, e.g., Pardridge. Austin (Tex.): Landes Bioscience; 2000-2013. Accordingly, a small molecule compound for use in accordance with present invention has preferably a molecular weight of less than 500 Dalton.

The present invention is based on the recent observation that the elevation of sTREM2 levels results in microglia survival and activation. Although it has long been controversially discussed, it is now assumed that microglia activation and survival in terms of treating neurological or neurodegenerative diseases have a beneficial effect on the disease and its progression (reviewed in Yeh et al., Trends Mol. Med. 23 (2017), 512-533). For example, a study by Hamelin and colleagues revealed a higher binding of the translocator protein TSPO, a marker for microglia activation, in AD patients with a slower rate of disease progression which supports the possibility that microglia activation exerts a positive effect (Hamelin et al., Brain 139 (2016), 1252-1264).

Experiments performed within the scope of the present invention surprisingly revealed that treatment of primary microglia cells with M1 muscarinic acetylcholine receptor (mAChR) agonists enhances the levels of sTREM2 released from the cells, which as discussed above results in microglia survival and activation. In line with these observations, further experiments performed in accordance with the present invention revealed that those agonists are also capable of enhancing the viability of human blood-derived macrophages. M1 mAChR agonists are therefore suitable for promoting microglia and/or macrophage survival and activation and thus useful in the treatment or prevention of neurological and neurodegenerative diseases and disorders which involve impaired microglia function via (soluble) TREM2.

Accordingly, in its broadest aspect, the present invention relates to a compound for use in treating a neurological or neurodegenerative disorder in a subject by promoting cellular viability and/or activation of microglia cells and/or macrophages, preferably wherein the compound is an agonist of human M1 mAChR. In principle, any M1 mAChR agonist may be used as a compound in accordance with the present invention. Suitable M1 mAChR agonists are described in European patent application EP 0 205 247 A2 and international applications WO95/03303, WO03/092580 and WO2010/084499 including compounds covered by formula (I), infra, their characteristics and methods of production, the disclosure content of which is incorporated by reference herein. In particular, the compound for use in accordance with the present invention is preferably selected from spiro and spiro quinuclidine compounds, respectively, for example form quinuclidine derivatives defined in any one of the claims of EP 205 247 A2 and preferably any one of those defined by formula (I) in the Table at page 7, most preferably compound AF1020B; aza spiro compounds defined in any one of the claims of WO95/03303 and preferably any one of those designated with the prefix "AF", most preferably compound AF102. AF150, AF267 or AF270; spiro compounds defined in any one of the claims of WO 03/092580 and preferably any one of those designated with the prefix "AF", most preferably compound AF267.

In a preferred embodiment, the compound for use in accordance with the present invention is selected from a compound having the formula (I):

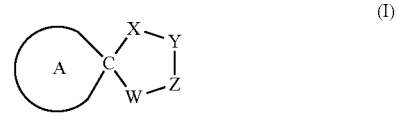

In formula (I) C denotes a spiro carbon atom shared by ring A and the ring containing X, Y, Z and W; A is selected from the group consisting of:

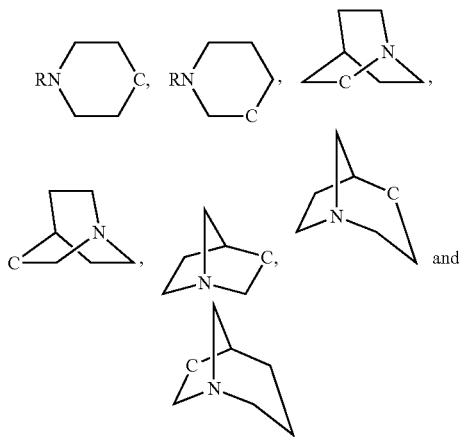

wherein R is selected from H, $C_{1-6}$-alkyl, and optionally substituted $C_{1-6}$-alkyl; X is —O—, —S—, or —NH—; Y is —$CR^1R^2$— or —$C(R^1)$=; Z is selected from the group consisting of —O—, —S—, =N—, —C(=O)—, or —C(=S)—; W is selected from the group consisting of —CH$_2$—, or —NH—; R, R$^1$, and R$^2$ are each independently selected from H, C$_1$-C$_8$ straight- or branched-chain alkyl. In addition, the compound of the invention is an enantiomer, diastereomer, racemate, tautomer, geometrical isomer, metabolite as crystalline or amorphous forms or pharmaceutically acceptable salt as crystalline or amorphous forms of formula (I).

Spiro compounds according to formula (I) have been shown to efficiently act as M1 mAChR agonists and are disclosed in European patent application EP 0 205 247 A2 and international applications WO95/03303, WO 03/092580 and WO2010/084499 wherein a variety of M1 mAChR agonists that can be used and covered by formula (I), their characteristics and methods of production are described and incorporated by reference herein. Methods of determining putative cholinergic agonists to muscarinic receptors and selectivity towards M1 receptor are also known to the person skilled in the art and described for example in the above-mentioned European and international patent applications.

The compounds for use in accordance with the present invention provide a protective effect on microglia and macrophage viability. Microglia and macrophage viability or survival, thereby, refers to the ability of the cells to maintain or recover viability. Accordingly, cell viability assays assess how healthy cells are. Diverse parameters are known to define cell viability, like the redox potential of the cell population, the integrity of cell membranes, or the activity of cellular enzymes such as esterases and the person skilled in the art is well aware of methods to assess cell viability including ATP test, calcein AM, clonogenic assay, ethidium homodimer assay, evans blue, fluorescein diacetate hydrolysis/propidium iodide staining (FDA/PI staining), flow cytometry, formazan-based assays (MTT/XTT), green fluorescent protein, lactate dehydrogenase (LDH), methyl violet, propidium iodide, resazurin, trypan blue, or TUNEL assay. An overview of commonly used methods is provided in the section Cell Viability Methods by Riss et al. (2013) in the eBook Sittampalam et al.: Assay Guidance Manual [Internet]. Bethesda (Md.): Eli Lilly & Company and the National Center for Advancing Translational Sciences; 2004—(available from: https://www.ncbi.nlm.nih.gov/books/NBK144065/). In this context, the compound for use in accordance with the present invention affects cell viability on the level of apoptosis, meaning that it results in suppression of apoptosis in microglia cells and macrophages, which can be assessed, for example, by annexin, caspase activation or TUNEL assays.

Figure 5:
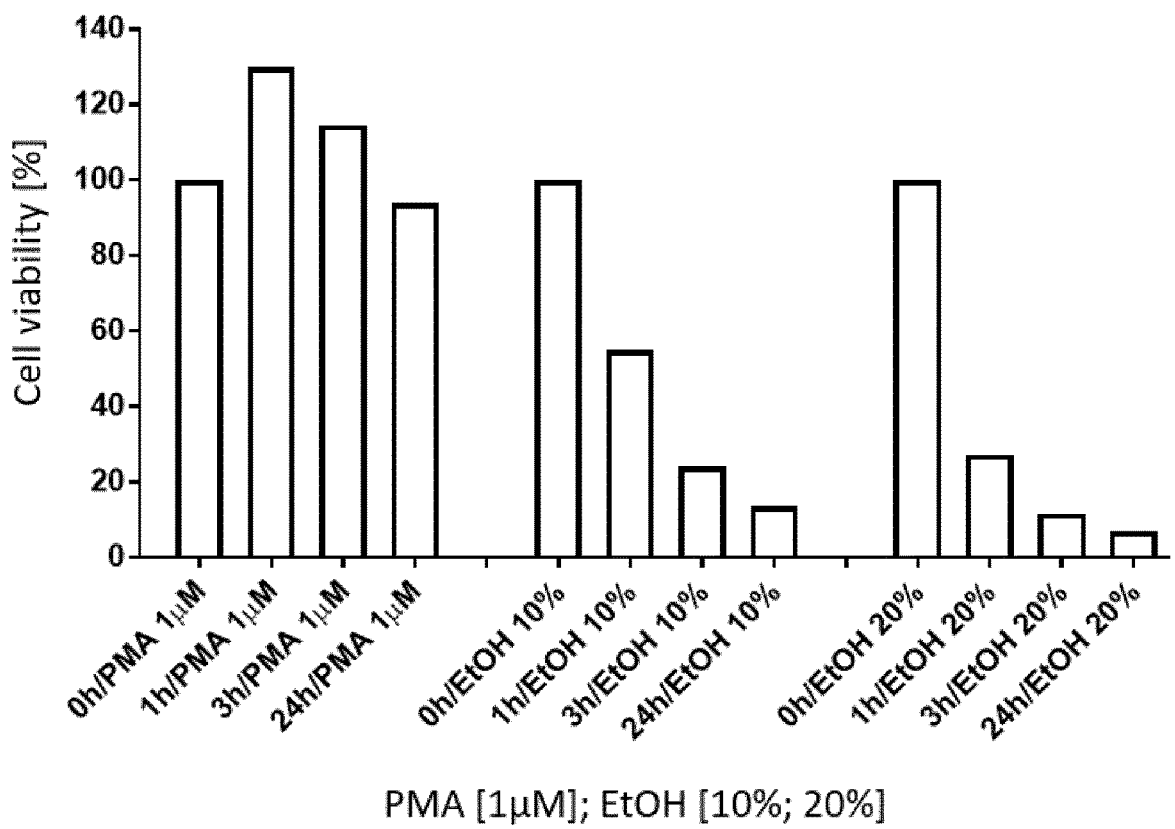
FIG. 5: Cell viability assessment of blood-derived human macrophages upon incubation with PMA, Ethanol (EtOH) or compounds NSC001 and AF102B. PMA (A), NSC001 (B) and AF102B (C) treatment results in an up to 30% increased cell viability after 24 hours compared to medium control. Application of Ethanol (A) to the cell medium rapidly decreases cell viability in a time- and concentration-dependent manner.
Figure 5:
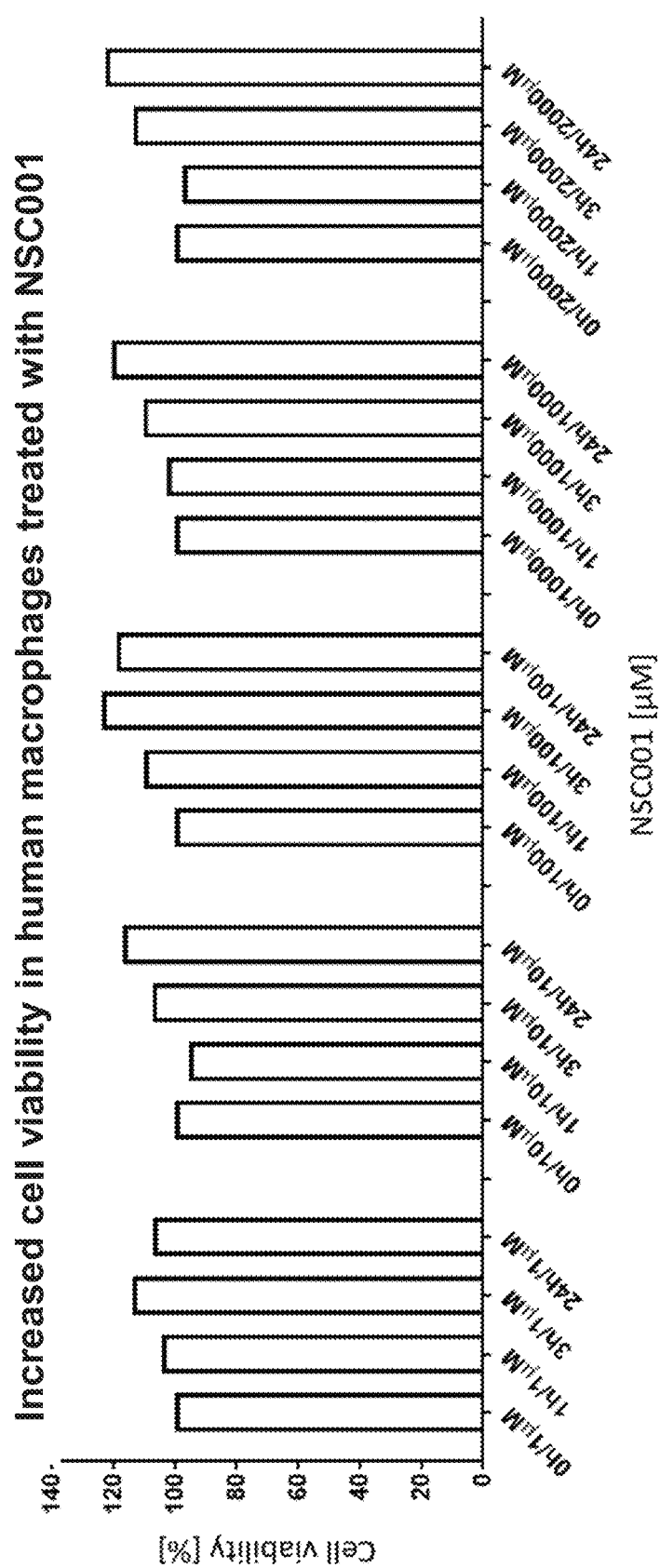
Figure 5:
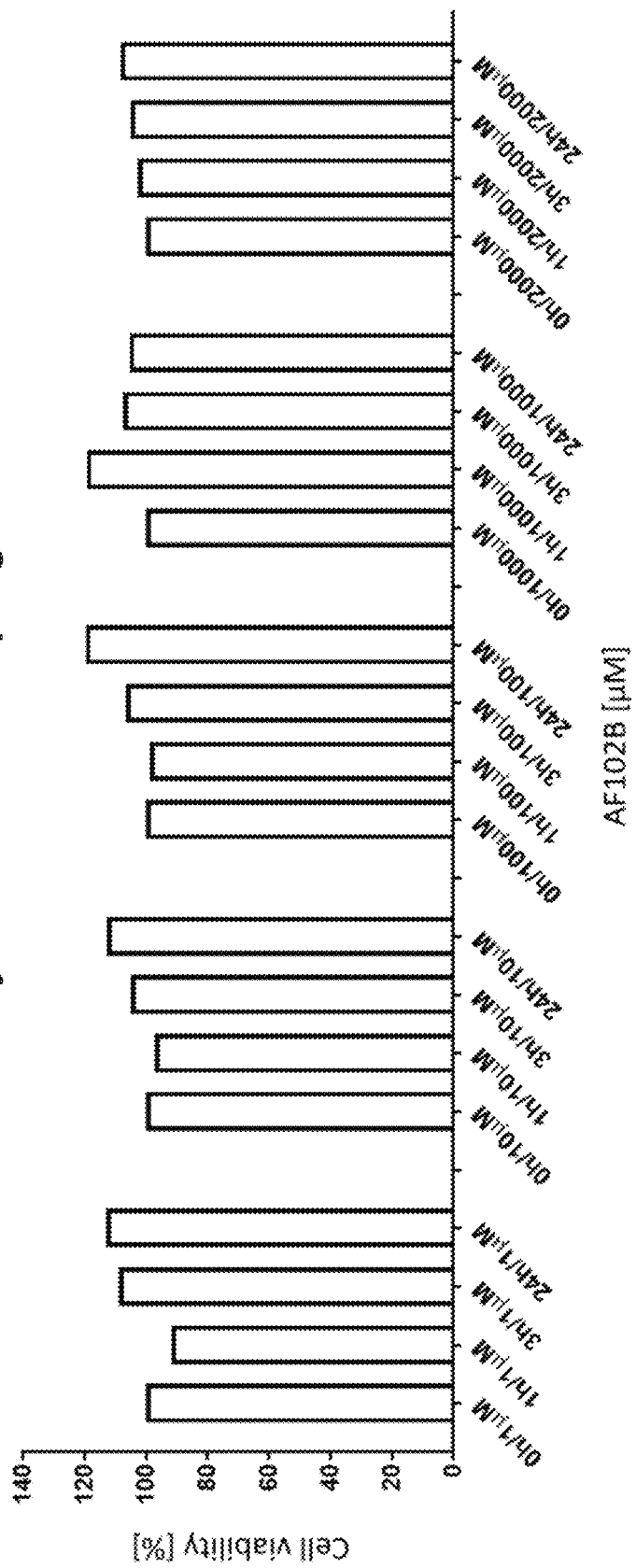

Cell viability analyses performed within the scope of the present invention revealed an increase in viability of human blood-derived macrophages upon treatment of the cells with the M1 mAChR agonists NSC001 and AF102B; see Example 5, FIG. 5. Microglia are understood to be the brain's resident macrophages and originate during embryogenesis form yolk sac-derived primitive macrophages persisting in the central nervous system into adulthood (reviewed in Ginhoux and Prinz, Cold Spring Harb Perspect Biol 7 (2015), a020537). Therefore, their positive effect on macrophages support the use of M1 mAChR agonists promoting microglia survival.

The compound for use in accordance with the invention preferably enhances microglia activation. Activated microglia release a wave of chemical mediators, including chemokines, cytokines, and proteases, all of which promote the neuroinflammatory milieu and stimulate the innate and adaptive immune response. In addition, microglia experience dramatic morphological changes from ramified cells to activated amoeboid microglia and up-regulate cell-surface receptors or other distinct receptors, e.g., for the removal of pathogenic organisms by phagocytosis. Accordingly, the person skilled in the art knows a variety of methods to analyze microglia activation, see, e.g., Davis et. al., Scientific Reports 7 (2017), 1576. However, microglia activation can be assessed by analyzing levels of inflammatory cytokines, such as interleukin-1β (IL-1β), interleukin-6 (IL-6), tumor necrosis factor α (TNF α), and interleukin-10 (IL-10) by qPCR following mRNA extraction from cells, tissues or other biological samples. In addition, an activated microglia morphology comprising an ovaloid cytoplasm and marked cellular hypertrophy can be detected and quantitatively evaluated with parameters like area, diameter, and perimeter following phalloidin staining.

The compound for use in accordance with the present invention is an agonist for the M1 mAChR. Signal transduction at the stimulatory M1 mAChR is via coupling with a G protein that is involved with mobilization of intracellular calcium. Agonist binding to these receptors results in activation of phosphoinositide phospholipase C with subsequent production of the second messengers, diaglycerol and inositol-1,4,5-triphosphate (IP$_3$). Stimulation of IP$_3$ ion channel receptors lead to release of intracellular calcium from the endoplasmatic reticulum. Accordingly, the activity of an M1 mAChR agonist can be assessed by a calcium mobilization assay (see Example 1) as well as by analyzing phosphoinositide (PI) hydrolysis (see Example 2). The compound of the invention which is an M1 mAChR agonist is capable of inducing an intracellular calcium mobilization and/or phosphoinositide (PI) hydrolysis via the human M1 mAChR. In particular, the compound preferably shows an intracellular calcium mobilization response in Chinese Hamster Ovary cells expressing the human M1 muscarinic receptor (CHOM1 cells) with respect to the cholinergic agonist carbachol (CCh) of at least 90%; and/or is capable of inducing PI hydrolysis in said CHOM1 cells at 1 mM with a maximal response of at least 50% of the maximal response obtained with 100 μM CCh; see Example 1 and 2.

In a preferred embodiment, the compound for use according to the invention has the formula (II):

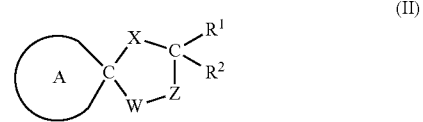

(II)

In formula (II) A is selected from the group consisting of:

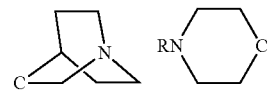

wherein R is CH$_3$; R$^1$ is H and R$^2$ is selected from CH$_3$ or CH$_2$CH$_3$; and Z is selected from the group consisting of =N—, —O— or —S—, —C(=O)—. In addition, the compound of the invention may be an enantiomer, diastereomer, racemate, tautomer, geometrical isomer, metabolite as crystalline or amorphous forms or pharmaceutically acceptable salt as crystalline or amorphous forms of formula (II).

As demonstrated in Examples 1 and 2, compound AF267B (NSC001) is a strong M1 mAChR agonist which efficiently induces calcium mobilization and PI hydrolysis. The compound has been generally described in U.S. Pat. Nos. 7,439,251 and 7,049,321 and in corresponding international application WO03/092580 as "AF267B" and is herein termed "NSC001" with the following chemical structure:

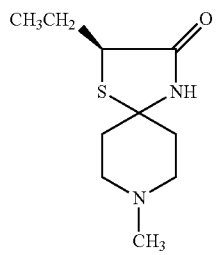

NSC001 has been shown to increase αAPPs, decrease Aβ levels and tau hyperphosphorylation, and block Aβ-induced neurotoxicity in vitro via M1 receptor mediated modulation of kinases (e.g. PKC, MAPK and GSK3β); see for review, e.g., Fisher, Curr. Alzheimer Res. 4 (2007), 577-580 and Fisher, J. Neurochem. 120 (2012), 22-33. AF267B was found to improve spatial memory in 3×Tg-AD mice and was associated with reduced Aβ and tau pathologies in the hippocampus and cortex (Caccamo et al., Neuron. 49 (2006), 671-682). Previously, AF267B formulated as a drug coined NGX-267 had been in phase II clinical trials for the treatment of Xerostomia and also in phase I clinical trials for the treatment of Alzheimer's disease and cognitive deficits in schizophrenia. Experiments performed within the scope of the invention surprisingly revealed that NSC001 induces sTREM2 levels in primary microglia cells (Example 3).

Therefore, in a preferred embodiment the compound for use according to the present invention the compound is (S)-2-ethyl-8-methyl-1-thia-4,8-diaza-spiro[4.5]decan-3-one (NSC001, AF267B) having the above formula.

In particular, it is preferred that the compound is a crystalline polymorph of NSC001 (AF267B), preferably Form II and most preferably Form Ill as disclosed in international application PCT/EP2017/075373; see, e.g., in particular page 16, last paragraph to page 17, second paragraph and Examples 7 to 13, 25, and 26 as well as FIGS. 6 to 8 and 11. As described therein the active pharmaceutical ingredient Form II can advantageously be obtained with high reproducibility and consistency and therefore proved particularly suitable to be manufactured according to cGMP. In addition, Form II is highly stable under dry storage conditions for at least two years and was tested in preclinical investigations and clinical trials (see Example 32 in PCT/EP2017/075373). To emphasize also Form III which is even more stable than Form//that was already used and will be used by us in the future clinical development.

In the experiments performed within the scope of the present invention, other compounds have been analysed besides NSC001. Therefore, in one embodiment of the invention the compound is cis-2-methylspiro[1,3-oxathiolane-5,3'-quinuclidine] hydrochloride (AF102B, Cevimeline), which has also been shown to be a strong M1 mAChR agonist (Example 1). AF102B has the following formula:

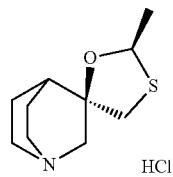

The compound is described in the international application WO03/092580 as "AF102B" and is prescribed in the USA and Japan for the treatment of Sjorgen's syndrome as Cevimeline (EVOXAC™). AF102B has been shown to elevate αAPPs, decrease Aβ levels and tau hyperphosphorylation, and block Aβ-induced neurotoxicity, in vitro, via M1 mAChR-modulation of kinases (e.g. PKC, MAPK and GSK3β); see for review, e.g., Fisher, Curr. Alzheimer Res. 4 (2007), 577-580. In addition, treatment with AF102B significantly decreased levels of Aβ in the CSF of AD patients (Nitsch et al., Ann Neurol 48 (2000), 913-918).

Recent studies emphasize the critical role of the triggering receptor expressed on myeloid cells 2 (TREM2) in neurodegenerative diseases; see for example Yeh et al., Trends Mol. Med. 23 (2017), 512-533 for review. Loss-of-function mutations in the TREM2 gene, which are often associated with neurodegenerative diseases, commonly lead to impaired microglia function. For example, it has been shown in mouse AD models, that TREM2 deficiency reduces the microglia response to Aβ plaque pathology: there is reduced number of microglia cells surrounding plaques and impaired activation of microglial gene expression. Therefore, the assumption is tempting that gain-of-function approaches, like TREM2 activation or the increase of TREM2 levels resulting in enhanced microglia function have a therapeutic benefit.

The fact that various mutations in the TREM2 protein are considered as risk factors for different neurological and neurodegenerative diseases renders microglia and TREM2 key players in disease progression. Specifically, the arginine 47 to histidine (R47H) substitution in the extracellular immunoglobulin domain significantly increases the risk for AD with an effect size similar to the well-characterized ApoE ε4 allele (Corder et al., Science 261 (1993), 921-923; Rebeck et al., Neuron. 11 (1993), 575-580).

One intriguing feature of the TREM2 protein is that it undergoes proteolytic cleavage by ADAM proteases, ADAM 10 and ADAM 17 (Feuerbach et el, Neurosci Lett 660 (2017), 109-114), releasing its ectodomain into the extracellular space as a soluble form (sTREM2) where it is abundantly detected in human plasma and CSF with increased levels in AD, multiple sclerosis (MS) and other neurological inflammatory diseases (Wunderlich et al., J. Biol. Chem. 288 (2013), 33027-33036; Kleinberger et al., Sci. Transl. Med. 6 (2014), 243ra86; Heslegrave et al., Mol. Neurodegener. 11 (2016), 1-7). For example, sTREM2 levels peak in the early symptomatic phase of AD and are positively associated with the amounts of total and phosphorylated tau in the CSF (Piccio et al., Acta Neuropathol. 131 (2016), 925-933; Suárez-Calvet et al., EMBO Mol. Med. 8 (2016) 466-476). Importantly, sTREM2 has been shown to mediate cell survival and inflammation in microglia as well as macrophages (Wu et al., J. Exp. Med. 212 (2015), 681-697; Zhong et al., J. Exp. Med. 214 (2017), 597-607).

More recently, Song. et al. (J. Exp. Med. 2018 Jan. 10. pii: jem.20171529. doi: 10.1084/jem.20171529. [Epub ahead of print]) using transgenic mice expressing the common variant (CV) of human TREM2 or the R47H TREM2 variant and lacking endogenous TREM2 in the SXFAD AD model could show that soluble TREM2 was found on neurons and plaques in CV—but not in R47H-expressing SXFAD brains, although in vitro CV and R47H were shed similarly via ADAM17 proteolytic activity.

Without intending to be bound by theory it is believed that these results make it plausible that sTREM2 represents a valuable therapeutic target for the treatment of neurological and neurodegenerative diseases, especially AD and other diseases associated with disturbed microglia function and/or deficiency in potent signalling capacity of the soluble cleaved TREM2 protein. For example, Bemiller et al. (Mol. Neurodegener. 12 (2017) doi: 10.1186/s13024-017-0216-6) describe that TREM2 deficiency leads to accelerated and exacerbated hyperphosphorylation and aggregation of tau in a humanized mouse model of tauopathy, suggesting that deficiency of microglial TREM2 leads to heightened tau pathology. Indeed, Jiang et al. (Inflammation. 2018 Jan. 23. doi: 10.1007/s10753-018-0735-5. [Epub ahead of print]) have shown that by manipulating TREM2 levels in microglia with a lentiviral-mediated strategy, TREM2 ameliorated the pathological effects of activated microglia on neuronal tau hyperphosphorylation via suppression of microglial inflammatory. Furthermore, microglia TREM2 deficiency appears to be involved in disorders such as amyotrophic lateral sclerosis, frontotemporal dementia, and Nasu-Hakola disease (NHD) suggesting that TREM2 deficiency may affect additional mechanisms independent of amyloid phagocytosis or plaque encapsulation, such as efficient corpse removal of dying cells or degenerating myelin; see for review see Condello et al., Biological Psychiatry 83 (2018), 377-387.

Accordingly, it is prudent to expect that in accordance with the present invention M1 mAChR agonists can be used to support TREM2 mediated neuroprotective functions of microglia and thus pave the way of treating various neurodegenerative diseases or reducing disease progression independent of the previously suggested rationale for their use in "cholinergic treatment" in AD based on the 'cholinergic hypothesis' which postulates that central pre-synaptic cholinergic deficits have a major role in the progressive cognitive dysfunction and some behavioral impairment associated with AD and that these cholinergic deficits can be restored via activation of the cholinergic system; see, e.g., Fisher, J. Neurochem. 120 (2012), 22-33 for review. Rather, in accordance with the present invention M1 mAChR agonists are advantageously used for microglia-mediated neuroprotection.

Thus, while previously M1 mAChR agonists have been specifically suggested for the treatment of AD dementia, i.e. patients suffering from at least episodic memory loss and other cognitive symptoms that are sufficient to interfere with the usual performance of accustomed instrumental activities of daily living (iADL) in order to restore cognitive and behavioral impairments, the present invention opens up a new window of the treatment of AD at the stage of predementia AD represented by prodromal AD, with episodic memory impairment that is insufficient to disrupt the performance of accustomed iADL or even at the preclinical stage, i.e. the treatment of subjects at a stage of AD that is not clinically expressed; that is, although the molecular pathology of AD is present in the brain, symptoms are absent. The use of preclinical signifies that this stage is to be detected by AD biomarkers, and not by (currently available) clinical methods. They may be further subdivided in asymptomatic at risk: cognitively normal individual with evidence of AD molecular pathology. It is not known whether progression to symptomatic AD will occur, and presymptomatic AD: individuals with autosomal dominant gene mutations which almost certainly will develop the disease; see, e.g., Draft guideline on the clinical investigation of medicines for the treatment of Alzheimer's disease and other dementias; EMA/CHMP/539931/2014 of Jan. 28, 2016 by the European Medicines Agency (EMA). In one embodiment of the present invention, the M1 mAChR agonist is for use in treating or preventing (i) patients with characteristic pathophysiologic changes of AD but no evidence of clinical impact and (ii) patients with characteristic pathophysiologic changes of AD and subtle detectable abnormalities on sensitive neuropsychological measures, but no functional impairment, and less preferred (iii) patients with characteristic pathophysiologic changes of AD, subtle or more apparent detectable abnormalities on sensitive neuropsychological measures, and mild but detectable functional impairment, and preferably not (iv) patients with overt dementia. Those categories (i) to (iv) correspond to stages 1 to 4 described by the U.S. Department of Health and Human Services Food and Drug Administration Center for Drug Evaluation and Research (CDER) Center for Biologics Evaluation and Research (CBER) February 2018 Clinical/Medical Revision 1 in the Draft Guidance as conceptually useful for the design and evaluation of clinical trials in different stages of AD.

The experiments of Zhong and colleagues included the in vitro and in vivo application of a fusion protein consisting of the sTREM2 extracellular domain and human IgG-Fc (sTREM2-Fc) to microglia cultures and mouse hippocampi exhibiting a protective effect on microglia cell viability as well as triggering inflammatory responses and microglia activation in vitro and in vivo. While an increase in sTREM2 levels results in suppression of apoptosis, proliferation of microglia cells remained unaffected. The use of small molecule compounds according to the invention in order to enhance sTREM2 levels provides advantages not only in the administration, which is much more convenient and efficient, but also in the substance as such, which is easier to produce, shows high stability and has been shown to be well tolerated and safe.

In line with the results provided by Zhong and colleagues, cellular viability analyses performed within the scope of the present invention revealed an increase in macrophage viability upon M1 mAChR agonist treatment (FIG. 5). Since, as described above, microglia and macrophages are closely related cell lines a parallel effect is to be expected on microglia cells upon M1 mAChR agonist treatment in accordance with the present invention.

Accordingly, in one embodiment of the invention, promoting the cellular viability and/or activation of microglia cells and/or macrophages is achieved by administering the compound in an amount effective to increase the level of soluble TREM2 (sTREM2). As shown in Examples 3 and 4 treatment of primary microglia cultures with a compound in accordance with the present invention, i.e. AF267B and AF102B significantly increases sTREM2 levels released by microglia cells (FIGS. 3B and 4A).

In addition, the studies by Zhong et al. revealed that the AD risk-associated TREM2 mutations R47H and R62H impair the function of sTREM2, namely reducing the overall capacity of sTREM2 to enhance cell viability and to trigger inflammatory responses in microglia (Zhong et al., J. Exp. Med. 214 (2017), 597-607) rendering an sTREM2-mediated therapy in patients with these genetic variations without beneficial effect.

Hence, in one preferred embodiment of the present invention, the subject to be treated is negative for a mutation that impairs the biological activity of sTREM2 and has at least one functional allele of the TREM2 encoding gene, respectively. Specifically, the mutation is R47H or R62H in the amino acid sequence of sTREM2. Accordingly, the invention comprises the screening of subjects for TREM2 mutations and the subsequent selection of subjects having at least one functional allele of the sTREM2 encoding gene. In other words, in one embodiment, subjects homozygous for a sTREM2-impairing mutation are preferably excluded from the treatment with the compounds in accordance with the present invention since no beneficial effect is to be expected. In general, sTREM2-impairing mutation relates to whether sTREM2 is released by microglia cells at all or whether the released protein is functional. As outlined by Yeh et al., various TREM2 mutations have been found affecting TREM2 function at different levels (Yeh et al., Trends Mol. Med. 23 (2017), 512-533). For example, mutations Y38C and T66M abolish TREM2 surface expression which renders sTREM2 release impossible. Accordingly, in one embodiment of the present invention, the mutation is Y38C or T66M in the amino acid sequence of the TREM2 gene. In addition, the person skilled in the art is well aware of methods to assess whether a mutation in the TREM2 gene affects sTREM2 function. As, for example, described by Zhong et al. a cDNA construct harbouring the relevant mutation can be constructed and purified as Fc fusion protein and tested for its ability to induce cell survival, suppression of apoptosis and/or increase of pro-inflammatory cytokines (Zhong et al., J. Exp. Med. 214 (2017), 597-607).

However, Zhong and colleagues showed that the mutations at positions R47H and R62H of TREM2 do not completely abolish sTREM2 function. Enhancing sTREM2 levels in patients carrying mutated sTREM2 by M1 mAChR agonist treatment in accordance with the present invention might, therefore, oppose the negative effect of the mutations and contribute to restoring overall sTREM2 function and microglia survival.

As described before, supra, compound NSC001 (as NGX267) and AF102B (as Cevimeline) have been tested in clinical trial or are, as in the case for AF102B, already used to treat dry mouth in Sjogren's syndrome patients. Furthermore, the international application PCT/EP2017/075373 teaches pharmacokinetics, safety and preliminary efficacy studies of NSC001 in humans; see Examples 32 and 33. Accordingly, in one embodiment of the invention the treatment comprises administering to the subject 1 mg to 100 mg of the compound, preferably 10 mg to 50 mg. However, in a further embodiment the compound is administered as an oral solution or an oral pill. Examples of how to formulate NSC001 as oral pills are also provided in PCT/EP2017/075373, e.g., in Examples 29 and 30.

Another embodiment of the present invention encompasses use of the compound for treating or preventing a condition or disease wherein microglia and/or macrophage function needs to be modulated by promoting microglia and/or macrophage survival and/or activation. Conditions are, for example, associated with impaired microglia and/or macrophage function. The disease or condition according to the invention is selected from the group consisting of brain amyloid-mediated disorders; GSK3β-mediated disorders; abnormalities in Wnt signalling; TREM2-mediated disorders; tauopathies; a tau protein hyperphosphorylation-mediated damage, dysfunction or disease; endogenous growth factor-mediated diseases; a combination of risk factors for Alzheimer's disease and/or one of the aforementioned diseases, e.g., autoimmune diseases and allergic disorders, head injury, oxidative stress, free radicals, apoptosis, inflammation, exogenous or endogenous toxins, excitotoxins, genetic predisposition, immune or autoimmune dysfunctions (e.g., lupus, multiple sclerosis, Sjogren's syndrome, chronic fatigue syndrome, fibromyalgia); dry mouth and dry eyes in Sjogren's syndrome, diseases states involving disturbances in which a cholinergic dysfunction has been implicated, Alzheimer's disease, Lewy Body dementia, frontotemporal dementia, Parkinson's disease, amyotrophic lateral sclerosis, multiple sclerosis, Nasu-Hakola disease (NHD, also known as polycystic lipomembranous osteodysplasia with sclerosing leukoencephalopathy, PLOSL), cerebral amyloid angiopathy, cerebral amyloidosis, vascular dementia, presenile dementia, progressive supranuclear palsy, transient global amnesia syndrome, autism related cognitive impairment, hyperlipidemia, hypercholesterolemia, vascular dementia, multi-infarct dementia (MID), stroke ischemia, MID combined with stroke/ischemia/head injury, combined MID and Alzheimer's disease, mixed Alzheimer's disease and Parkinson's disease, human head injury, age-associated memory impairments, mild cognitive impairment (MCI), MCI conducive to Alzheimer's disease, bipolar disorder, mania, acute confusion disorder, attention deficit disorder, hallucinatory-paranoid states, emotional and attention disorders, post-operative delirium (anticholinergic syndrome following general anaesthesia), sepsis and septic delirium in intensive care units, antagonism of adverse effects (such as xerostomia, anomia, memory loss and/or confusion, psychosis) of tricyclic antidepressants or of certain drugs (e.g., trihexyphenidyl) used in treating schizophrenia and Parkinson's disease, schizophrenia, bipolar disorder, mania, tardive dyskinesia, congenital ornithine transcarbamylase deficiency, ollivopontocerebral atrophy, alcohol withdrawal symptoms, Huntington's chorea, Pick's disease, Friedrick's ataxia, Gilles de la Tourette disease, and Down's syndrome.

As reported by Zheng and colleagues TREM2 promotes microglia survival by activating the Wnt/β-catenin signalling pathway demonstrating a critical role of a TREM2-mediated Wnt/β-catenin pathway in microglia viability and suggest that modulating this pathway therapeutically may help to combat the impaired microglial survival and microgliosis associated with, for example, AD (Zheng et al., J. Neurosci. 37 (2017), 1772-1784).

In another embodiment of the present invention the compound is comprised within a pharmaceutical composition used for the treatment of a neurological or neurodegenerative disorder by promoting microglia and/or macrophage survival and/or activation. The pharmaceutical composition comprises at least one pharmaceutically acceptable excipient or carrier in addition to the compound. For example, the compound for the pharmaceutical composition is formulated by the addition of water or by the process comprising the steps:

(i) adding $H_2O$ to the compound, preferably to obtain an 0.1 mol/l solution,
(ii) adding 1N HCl, preferably to a concentration of 0.1 mol/l,
(iii) vortexing for several seconds,
(iv) adding $H_2O$, preferably to obtain an 0.05 mol/l solution,
(v) vortexing for several seconds resulting in a clear solution,
(vi) adding buffer to obtain a 0.01 mol/l solution, and
(vii) diluting the solution in buffer to the desired concentration In addition, in a further embodiment the pharmaceutical composition is a formulation of a crystalline polymorph of the compound, which is suitable for oral administration, and wherein the formulation is (i) directly compressed into tablets; or (ii) mixed with one or more excipient(s) (pregelatinized starch, microcrystalline cellulose, colloidal silicon dioxide, and stearic acid) and the mixture is filled in size 4, white opaque, hard gelatin, two-piece capsules to provide 5 mg or 10 mg of the compound per capsule, which can be used as an oral formulation for immediate release in the gastrointestinal tract.

Oral tablets can be manufactured by direct compression of crystalline polymorph of the compound, for example, NSC001 anhydrous crystalline Form II. It is known generally that the advantages of direct compression include few manufacturing steps involved, physical stability and elimination of heat and moisture. Direct-compression tablets according to the invention can additionally contain binders, disintegrants, and colorants such as are familiar to those knowledgeable in the art. In another embodiment, pre-manufactured oral capsules contain crystalline polymorph of the compound, for example, NSC001 crystalline Form I//along with excipients. Following compression of the tablets, or closure of the capsules, pharmaceutically acceptable coatings can be applied to these presentations of the invention in order to further modify release characteristics of the active agent in the gastrointestinal tract. The selection of the optimal release site depends on the type of disease, the intended plasma peak concentrations, the intended plasma time/concentration-profile and the intended time/concentration profile at the target site. Further examples for pharmaceutical compositions comprising crystalline polymorphs of NSC001 are described in the international application PCT/EP2017/075373; see, e.g., at page 25, last paragraph to page 26, second paragraph.

In line with studies performed by Hamelin and colleagues suggesting a protective role of microglia activation especially in early stages of AD, the compound of the invention is suitable for treating early or even preclinical stages of AD or other neurological diseases (Hamelin et al., Brain 139 (2016), 1252-1264). Furthermore, in later stages of neurodegenerative diseases, like AD, when sustained microglia activation and chronic neuroinflammation rather have a detrimental effect on the disease, it may beneficial to apply an anti-inflammatory agent in addition to the compound or the pharmaceutical composition described above in order to maintain microglia survival while suppressing neuroinflammation. Accordingly, in one embodiment of the invention the treatment or the pharmaceutical composition, additionally, comprise an anti-inflammatory agent.

In accordance with the present invention, pharmaceutical compositions based on crystalline polymorphs of the compound that can be used to treat or prevent the above-mentioned diseases and disorders which are responsive to stimulation of microglia and/or macrophage viability and activation may be prepared in different presentations, and may be administered using different routes of administration. Guidance regarding formulations that are suitable for various types of administration can be found for example in Remington: The Science and Practice of Pharmacy (2000) by the University of Sciences in Philadelphia, ISBN 0-683-306472. Therefore, the present invention also provides methods for administering drugs to treat or prevent diseases or conditions which are responsive to agonistic stimulation of microglia survival and activation.

Thus, in another embodiment the invention relates to a method for the prevention or treatment of a neurological or neurodegenerative disorder comprising administering to a subject in need thereof the compound or the pharmaceutical composition in a therapeutically effective amount to increase the level of sTREM2. In addition, the invention relates to a method of maintaining, promoting and/or enhancing microglial survival in a subject in need thereof comprising administering to the subject the compound or the pharmaceutical composition in a therapeutically effective amount.

In a further aspect the present invention encompasses an in vitro method of maintaining, promoting and/or enhancing cellular viability and/or activation of microglia cells comprising contacting a cell culture comprising microglia cells with the compound of the invention.

In another embodiment the invention encompasses a method of monitoring efficacy of the treatment of a subject suffering from or disposed to develop a neurodegenerative or inflammatory disease or disorder with a compound of the invention, comprising
  (a) assaying the level of sTREM2 in a sample of the subject's body fluid, preferably CSF at a specified time interval following (preferably peripheral) administration of the compound, wherein the compound can trigger the release of sTREM2 to alter the level of and net efflux of sTREM2 from brain to the body fluid;
  (b) comparing the assayed level of sTREM2 in the body fluid sample to a reference standard; wherein the difference or similarity between the level of sTREM2 in the body fluid sample and the reference standard correlates with the level of sTREM2 in the brain of the subject.

As also described before, levels of sTREM2 in the CSF are altered in patients with different neurological and neurodegenerative diseases and sTREM2 is considered as a potential biomarker for microglia activity in early-stage AD (Piccio et al., Acta Neuropathol. 131 (2016), 925-933; Suárez-Calvet et al., EMBO Mol. Med. 8 (2016), 466-476). Therefore, monitoring the levels of sTREM2 during the treatment of a subject with the compound of the invention is suitable to assess the efficacy of the treatment. Levels of sTREM2 can be determined by a variety of methods, for example, by the sTREM2 ELISA established by Kleinberger et al., Sci. Transl. Med. 6 (2014), 243ra86.

As mentioned, the present invention inter alia is based on the surprising observation that agonists of human M1 mAChR agonist are capable of stimulating sTREM2 release from mammalian, preferably human or mouse microglia cells. Therefore, the compound for use according the present invention preferably has a pronounced activity of elevating the level of sTREM2 secretion such as shown for NSC001 (AF267B) and AF102B. Since not every M1 mAChR agonist may be capable of stimulating the release of sTREM2 from a mammalian microglia cell, the compound for use in accordance with the present invention is preferably verified for this activity in an appropriate cellular in vitro assay such as described in Examples 3 and 4, or through in vivo animal models such as transgenic mice expressing the common variant (CV) of human TREM2 described in Song et al. (2018), supra.

Accordingly, the invention encompasses a method of preparing a pharmaceutical composition comprising an M1 mAChR agonist having the effect of enhancing microglial and/or macrophage survival and/or activation; said M1 mAChR agonist having been contacted in vitro with a microglia cell and/or macrophage, and determined to stimulate secretion of sTREM2 from the mammalian microglia cell and/or macrophage, wherein the ability of the M1 mAChR agonist to stimulate sTREM2 release from the mammalian microglia cell and/or macrophage is indicative of the agonist being a compound useful for treating or preventing a condition ameliorated by enhancing microglial and/or macrophage survival and/or activation; said method comprising admixing the agonist with a pharmaceutically acceptable carrier.

Both sTERM2 and TREM2 have been associated with microglia activation and TREM2 expressing microglia have been shown to surround and encase amyloid fibrils resulting in neuroprotection. Haploinsufficiency or lack of TREM2 reveals enhanced neuritic dystrophy derived from Amyloid-β and diminished microglia activation upon neuronal injury (Zhong et al., J. Exp. Med. 214 (2017), 597-607; Wang et al., J Exp Med. 213 (2016), 667-75; Mazaheri et al., EMBO Rep. 18 (2017), 1186-1198; Yuan et al., Neuron 90 (2016), 724-39; Condello et al., Nat Commun. 29 (2015), 6176). Similarly, animal data is in line with impairment of TREM2 function by reducing microglia response to amyloid pathology described in postmortem AD tissue expressing the R47H TREM2 variant (Krasemann et al., Immunity 47 (2017), 566-581). Moreover, the AD risk mutation H157Y TREM2, located at the sTREM2 cleavage site, has been shown to enhanced release of sTREM2. Concomitantly, increased sTREM2 release is lowering cell surface TREM2 and reduces microglia phagocytotic activity (Jiang et al., Neurobiol Aging 42 (2016), 69-79; Schlepckow et al., EMBO Molecular Medicine 9 (2017), 1356-1365; Thornton et al., EMBO Mol Med 9 (2017), 1366-1378). In contrast, treatment of mammalian microglia cell with the said M1 mAChR agonists, AF267B and AF102B, present with unaltered levels of total TREM2 despite release of sTREM2, thereby preserving the beneficial effect of TREM2 on microglia activation.

This method is suitable to assess whether an M1 mAChR agonist is capable of enhancing sTREM2 levels and consequently microglia and/or macrophage viability and/or activation. Accordingly, as described in the Examples 3 and 4 and the corresponding methods primary microglia cultures are treated with an M1 mAChR agonist. After incubation with the compound for a defined time, for example, 24 hours, the amount of sTREM2 is determined in the cell culture medium. Alternatively or in addition, cell viability and/or activation can be analysed in these cultures as described above.

To sum up, in view of the results obtained from the experiments described in the appended Examples, the compound for use in accordance with the present invention as disclosed herein is preferably characterized in being capable of (i) stimulating sTREM2 secretion from mammalian, preferably human or mouse microglia cells, preferably when assessed in accordance with Example 3 or 4;
(ii) inducing an intracellular calcium mobilization response, preferably when assessed in Chinese Hamster Ovary cells expressing the human M1 mAChR (CHOM1 cells) with respect to carbachol (CCh) of at least 90% in accordance with Example 1; and/or
(iii) inducing phosphoinositide (PI) hydrolysis, preferably in said CHOM1 cells of (ii) at 1 mM with a maximal response of at least 50% of the maximal response obtained with 100 μM CCh in accordance with Example 2.

Preferably, the compound for use in accordance with the present invention displays all three (i) to (iii) properties and/or displays one, two or preferably all three of those properties to substantially the same effect as NSC001 or AF102B, i.e. at substantially at least the same concentration or no more than about 10% less activity of either NSC001 or AF102B. Thus, in a particularly preferred embodiment the compound for use in accordance with the present invention displays substantially the same activity profile towards features (i) to (iii) as NSC001 and/or AF102B. Indeed, the present invention generally relates to the use of a small molecule compound for increasing the level of soluble triggering receptor expressed on myeloid cells 2 (sTREM2) in vitro or in vivo.

In a particular preferred embodiment the compound for use in accordance with the present invention displays the activity defined in any one, two or all of features (i) to (iii) above at a concentration of about 100 μM (microM), preferably at about 10 μM, and more preferably at a concentration of about between 1 to 10 μM and most preferably at a concentration of about between 1 to 5 μM as demonstrated for NSC001 while AF102B is active from 10-100 microM.

Next to these in vitro methods, the person skilled in the art is also aware of in vivo animal studies to assess whether an M1 mAChR agonist according to the invention is capable of promoting microglia and/or macrophage viability and/or activation. For example, it may be analysed how a compound administered to a laboratory animal affects microglia and/or macrophage activation by analysing levels of pro-inflammatory cytokines or microglia morphology in the hippocampi of treated animals as described by Zhong et al., J. Exp. Med. 214 (2017), 597-607. Furthermore, animal disease models can be used to further determine the compounds effects on disease progression.

EXAMPLES

The following Examples help illustrate embodiments of the invention. It will be appreciated that the invention is not intended to be limited by the foregoing description, which is meant to help illustrate embodiments of the invention.

Materials and Methods

NSC001 (AF267B) (mp. 134° C.; purity by HPLC (achiral) 99.9%; purity by HPLC (chiral) 99.7-100% and AF102B (purity by HPLC>99%) were used in this study. All other compounds were of analytical grade and were purchased from commercial sources.

Compound Formulation

The compounds NSC001 and AF102B are formulated in an aqueous solution. For example, a 0.01 M solution of NSC001 is obtained by the following protocol:

(1) 46 μl $H_2O$ are added to 1 mg of AF267B (0.004666 mmol),
(2) 4.66 μl 1N HCl are added and the solution is vortexed well for several seconds in vortex,
(3) 46 μl $H_2O$ are added and the solution is vortexed well for several seconds in vortex in order to completely dissolve the solid, resulting in a clear solution,
(4) to obtain a 0.01 M solution 369.91 μl buffer (e.g., DMEM) are added and the solution is swirled for several seconds.

The solution of the compound can be stored at 4° C. for one week and is diluted to the required concentration with the appropriate buffer for each specific test.

Cell Culture of CHOM1

Cells were routinely cultured in Dulbecco's Modified eagle medium (Gibco, UK) supplemented with 10% fetal bovine serum (FBS), 1×MEM non-essential amino-acid, 584 mg/ml Glutamine, 100μ/ml Penicillin, 0.1 mg/ml Streptomycin, 25 μg/ml Amphotericin B and 100 μg/ml G418

(Biological industries, Israel). Cells were kept in a humidified atmosphere at 37° C. in 5% $CO_2$ and were passaged twice weekly by 2.5 mg/ml trypsin-EDTA (0.02%) solution (Biological industries, Israel) and re-suspended in fresh media.

Isolation of Primary Microglia

Primary microglia were isolated from C57BL6 pups (P4-6). Mouse brains were prepared by removing the cerebellum and the meninges. Brain tissue was dissected and single cell suspension was sorted via CD11b Microbeads (Milteny Biotec) to obtain primary microglia. Cells were plated at $4 \times 10^5$ cell/ml in 24 well plates and cultured for 24 hours in DMEM supplemented with 10% FBS and 1% Penicillin/Streptomycin.

Example 1: M1 mAChR Agonists NSC001 (AF267B) and AF102B Show High Calcium Mobilization Calcium fluorescence measurements were performed using a NOVOstar plate reader with an injector and a pipetting system (BMG Labtech, Ortenberg, Germany). At the day before the experiment Chinese Hamster Ovary (CHO) cells expressing human M1 mAChR subtypes (CHOM1) were harvested and rinsed with culture medium (see section "cell culture", supra) without Phenol red and evenly plated into black-wall clear optical bottom 96-well plate (Nunc, Rochester NY, USA) at a density of 40,000 cells/well. Growth medium was removed and 80 µl of loading buffer, containing 2.5 mM probenecid, was carefully added (loading buffer prepared according to FLUO-4 NW calcium assay kit manual). The cell plate was incubated at 37° C. for 30 minutes; then at room temperature for an additional 30 minutes. EGTA (10 µl of 50 mM dissolved in HBSS) was added automatically to each well using the NOVOstar injector system followed by shaking of 1 minute (1 mm width, 600 rpm) and then incubated for another 10 minutes. HBSS alone or test compounds dissolved in HBSS were then added (10 µl) sequentially into separate wells using the NOVOstar robotic pipettor system. Fluorescence intensity was measured at 0.5 second intervals, for 30 second for each well, using an excitation wavelength of 485 nm (bandwidth 10 nm) and emission of 520 nm (bandwidth 10 nm), cut-off 515 nm. All assays were carried out in triplicates in three independent experiments. Competition curves and $EC_{50}$ values were derived using the GraphPad Prism software program, version 3.0. As shown in FIG. 1 cells treated with NSC001 (AF267B) and AF102B showed a high calcium mobilization response with respect to CCh (113% and 101%, respectively).

Example 2: M1 mAChR Agonists NSC001 (AF267B) and AF102B are Effective in Phosphoinositide Hydrolysis Rat pheochromocytoma cells (PC12) transfected with rat M1 muscarinic receptor (PC12M1) or CHOM1 cells were seeded in 24-well plates at a density of $4-8 \times 10^5$ cells/well. A day later, a fresh growth medium containing 1 µCi/ml [$^3$H]inositol (myo-[2-$^3$H(N)] 22 Ci/mmol; purchased from NEN, Boston, MA) was added for 18-24 h (overnight). Then, the medium was removed and the cells were washed twice followed by pre-incubation (10 min) with serum-free medium containing 20 mM Hepes pH 7.4 and 10 mM LiCl. Subsequently, a 20 min incubation was employed with various concentrations of NSC001 and CCh, respectively. Basal activity was determined in cells that were incubated in parallel without the tested compounds. Termination of the assay was carried out by aspirating the media and adding 0.5 ml 2% trichloroacetic acid (TCA) followed by agitating the cells in the cold for 30 min. The TCA extracts were transferred to anion-exchange columns, washed five times with 5 mM inositol, once with 5 ml 5 mM $Na_2B_4O_7$ in 60 mM formic acid, and the total IPs were eluted with 3 ml 1 M $NH_4COOH$ in 0.1 M formic acid. The effluent was collected into scintillation vials and the radioactivity was measured using liquid scintillation counter, 1214 Rackbeta LKB Wallac. Data is expressed as percent of the activity obtained for 100 µM CCh (considered as the maximal increase) after subtracting the basal counts.

Figure 2:
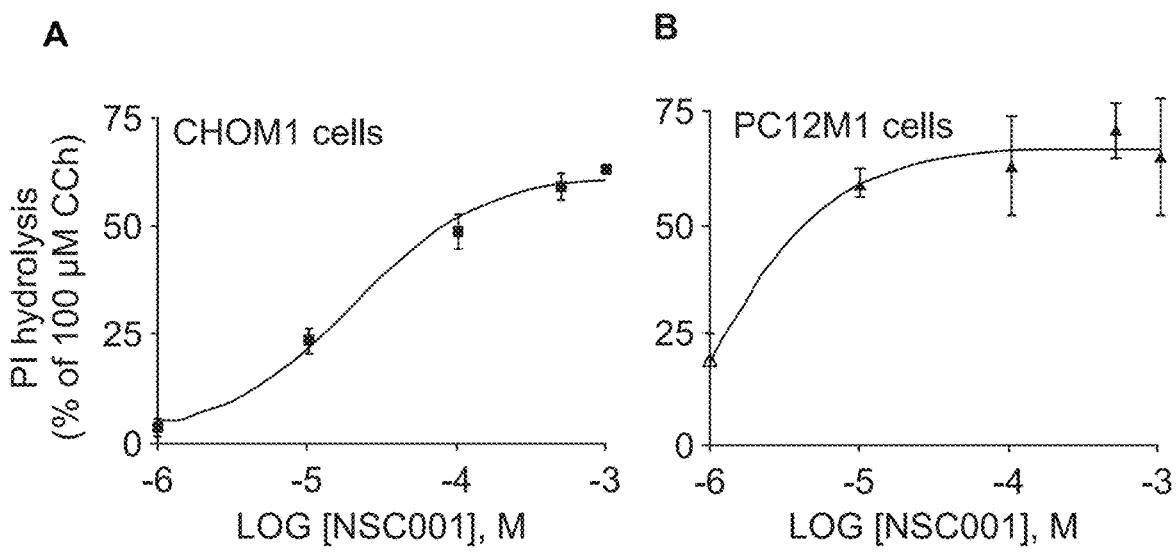
FIG. 2: Phosphoinositide (PI) hydrolysis induced by the compound NSC001 in CHOM1 cells (A) and PC12 cells expressing the M1 mAChR (PC12M1; B). NSC001 efficiently induces PI hydrolysis in CHOM1 (A) as well as PC12M1 cells (B) resulting in a maximal response (at 1 mM) of 63±1% relative to CCh (obtained with 100 μM CCh). PI hydrolysis in CHOM1 cells induced by AF102B is 43% relative to CCh.

As can be seen in FIG. 2, NSC001 was efficacious in activating the M1 mAChR subtype in CHOM1 (FIG. 2A) as well as in PC12M1 (FIG. 2B) cells. Actually, the maximal response of NSC001 (at 1 mM) was 63±1% of the maximal response (obtained with 100 µM CCh) in CHOM1 cells. The EC50 of NSC001 was 19 µM. AF102B is less effective than NSC001 as shown in the Table in FIG. 2.

Figure 3:
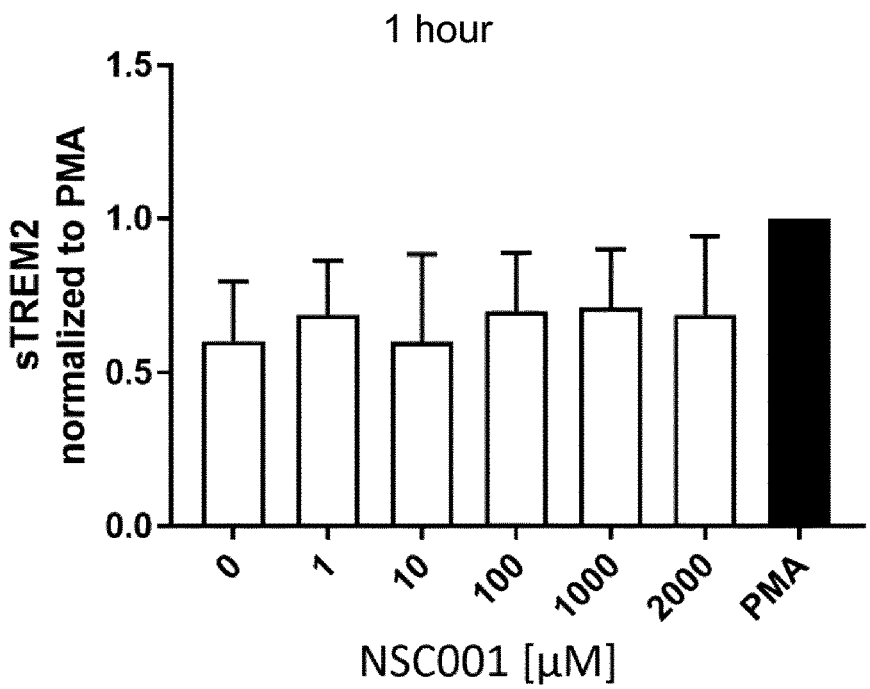
FIG. 3: Analysis of soluble and total TREM2 levels (sTREM2 and tTREM2) in primary microglia cultures upon NSC001 treatment. After 1 hour of treating cells with NSC001, no effect on sTREM2 levels in medium (A) as well as cellular tTREM2 levels (C) is observed. NSC001 treatment for 24 hours results in a significant increase of sTREM2 levels in a concentration dependent manner. (B). Concomitantly, tTREM2 levels remain constant after 24 hours of treatment (D). sTREM2 level are normalized to Phorbol myristate acetate (PMA 1 µM). N=4-6 repeats. Error Bar in SEM.
Figure 3:
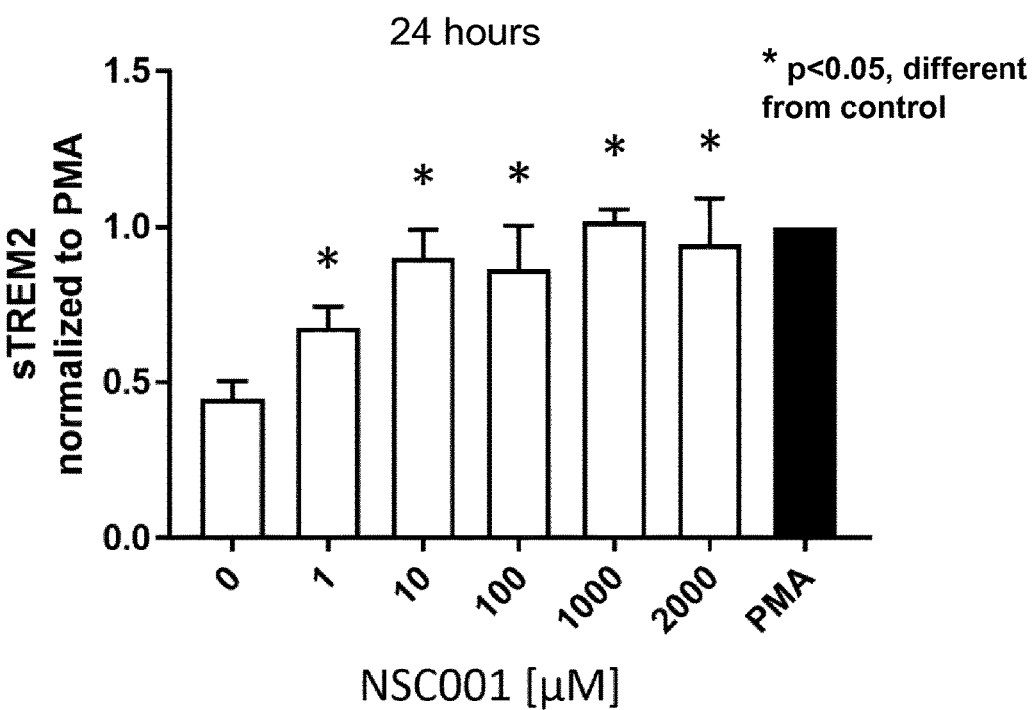
Figure 3:
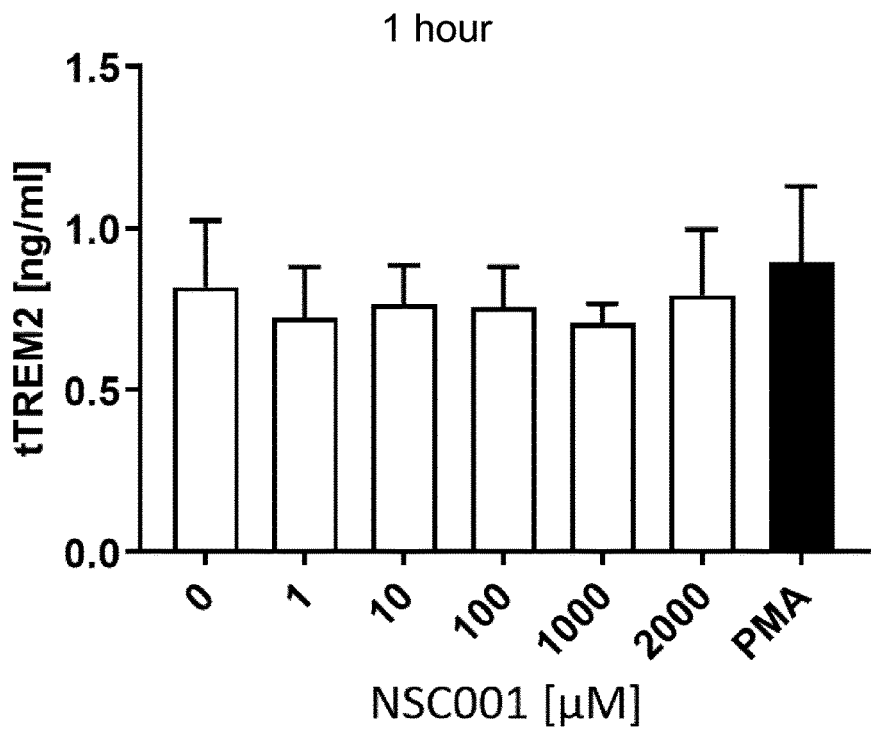
Figure 3:
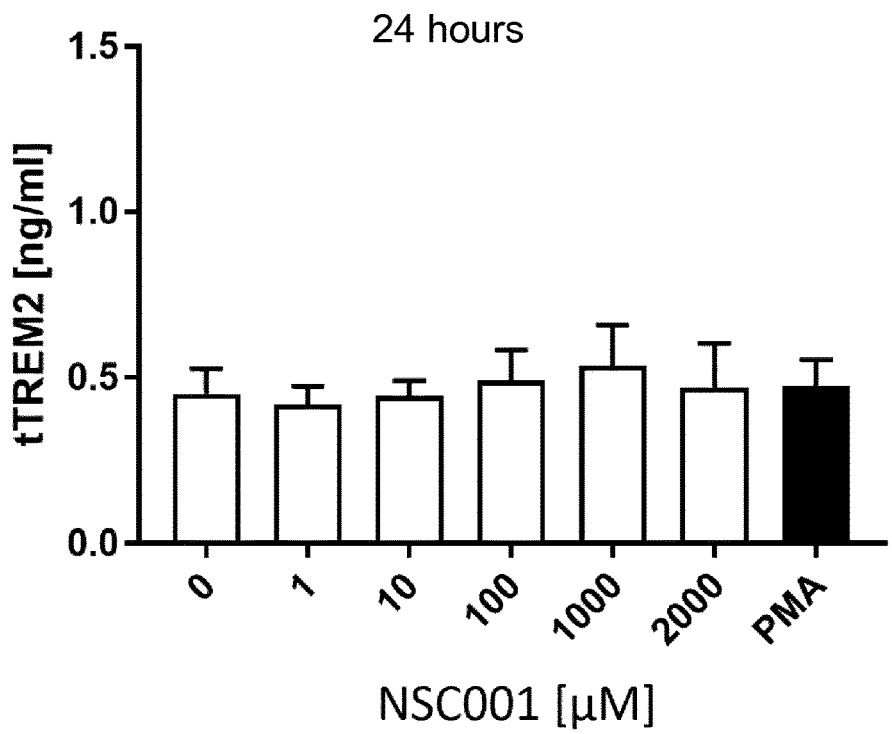

Example 3: M1 mAChR Agonists NSC001 (AF267B) and AF102B are Capable of Inducing Enhanced Soluble TREM2 Levels in Primary Microglia Mouse primary microglia were prepared from mice postnatal day 4-6 according to standard protocols (Neuronal Tissue Dissociation Kit (P), 130-092-628 and CD11b Microbeads, 130-093-634; Miltenyi Biotec 5 GmbH, Germany) and seeded in 24-well plates at a density of $4 \times 10^5$ cells/well. After one day, cell medium was removed and cells were washed once with PBS. Subsequently, cell were treated with compound NSC001 (0-2000 µM) in FBS-free DMEM for 1 or 24 hours. Termination of the assay was carried out by collecting the media and concomitant concentration via centrifugal filter units (Amicon, Z648027-24EA, Sigma 10 Aldrich, Ireland). Cell lysis was performed by adding RIPA lysis buffer (RIPA buffer, R0278, Sigma-Aldrich Co LLC, USA) followed by agitating the cells at 4° C. for 30 min. Primary microglia cell lysates and concentrated cell medium were analyzed for soluble TREM2 (sTREM2; FIG. 3A,B) and total TREM2 (tTREM2; FIG. 3C,D) levels by ELISA (CSBEL024405MO, Cusabio Life Science, China). As shown in FIG. 3, NSC001 treatment resulted in a significant increase of TREM2 processing and release of sTREM2 into the medium after 24 h (FIG. 3B) compared to 1 h treatment with no alteration detected (FIG. 3A). Total TREM2 levels remained constant after 1 h and 24 h of NSC001 treatment at different concentrations (FIG. 3C,D). In addition, it was shown that NSC001 is a highly potent compound able to increase sTREM2 levels at a concentration of 1 µM comparable to PMA (FIG. 3B). Further increase in sTREM2 exceeding the levels detected upon PMA treatment (1 µM) was not observed with higher concentrations of NSC001 (100-2000 µM).

Figure 4:
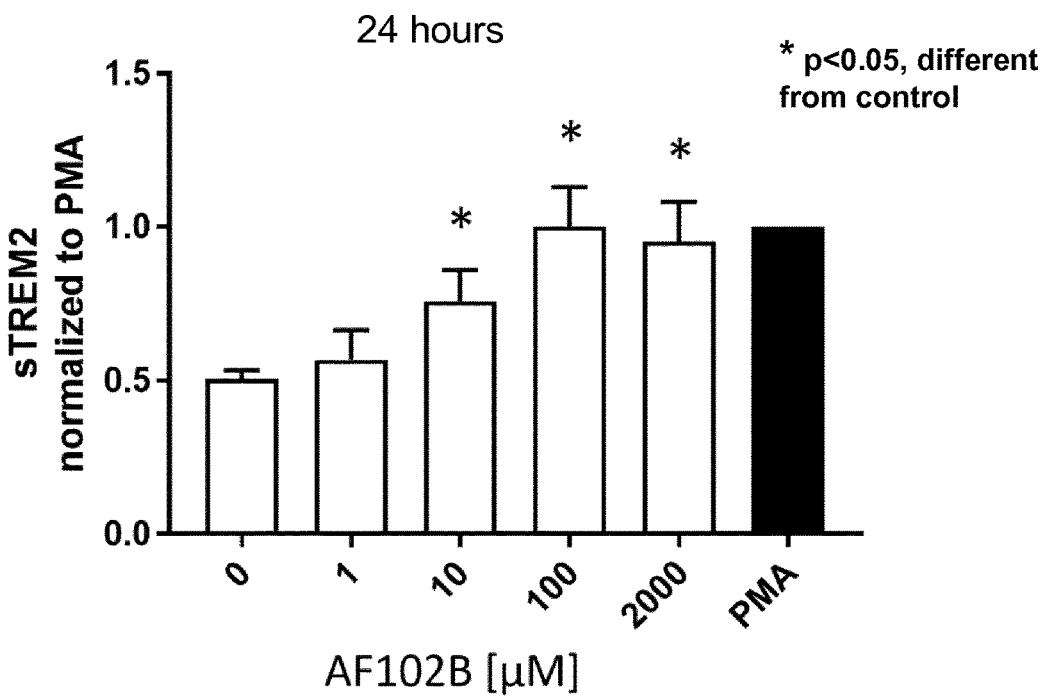
FIG. 4: Analysis of soluble and total TREM2 levels (sTREM2 and tTREM2) in primary microglia cells upon AF102B treatment for 24 hours. Treatment of cell with AF102B significantly enhances sTREM2 levels (A), whereas tTREM2 levels are unaffected (B). sTREM2 level are normalized to Phorbol myristate acetate (PMA 1 µM). N=4-6 repeats. Error Bar in SEM.
Figure 4:
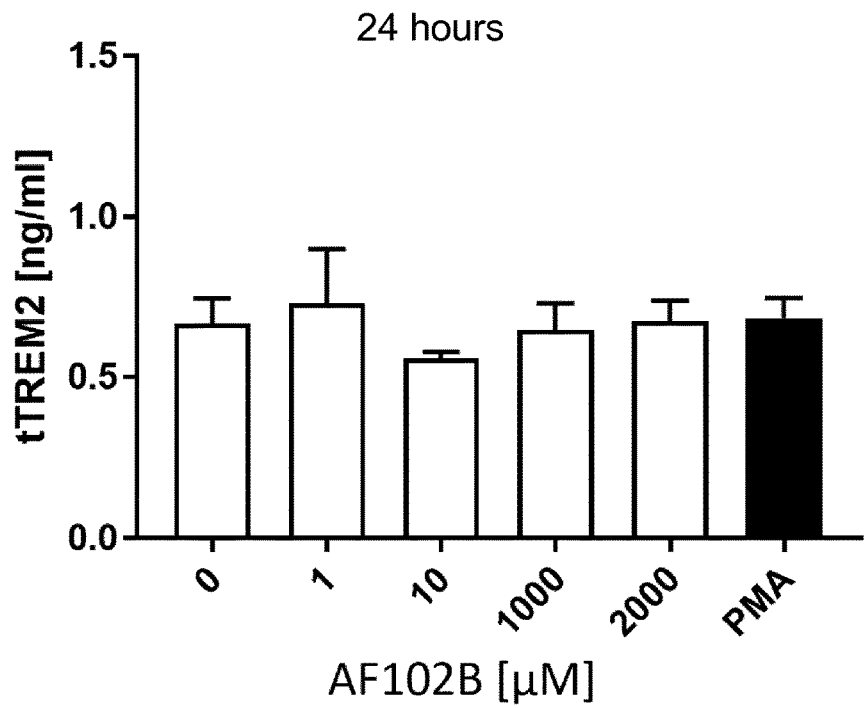

Example 4: M1 mAChR Agonist NSC001 (AF267B) and AF102B Treatment does not Affect Total TREM2 Levels in Primary Microglia Primary microglia cells were treated as described in Example 3. sTREM2 and tTREM2 levels were determined after 24 h of incubation of the cells with compound AF102B (FIG. 4). As depicted in FIG. 4A, compound AF102B was capable of inducing sTREM2 levels in primary microglia cultures. Comparable to treatment with compound NSC0001, tTREM2 levels were not affected by treating the cells with compound AF102B (FIG. 4B).

In summary, the results of Example 3 and 4 are consistent with the ones provided in Example 1 and 2 where it is shown that NSC001 and AF102B are strong M1 agonists.

Example 5: M1 mAChR Agonist NSC001 (AF267B) and AF102B Treatment Increases Cell Viability in Human Macrophages Human blood-derived macrophages were isolated from buffy coat via standard protocols (Monocyte isolation Kit, 130091153, Miltenyi Biotec GmbH, Germany) and differentiated for 9 days in M-CSF medium (Ser. No. 12/065,074, Thermo Fisher, Switzerland,) supplemented with 125 ng/ml human GM-CSF (130093864, Miltenyi Biotec GmbH, Germany) to induce M1 macrophage differentiation. Upon differentiation, cells were harvested and re-seeded at 1 Mio cells per 24-well. After 24 hours cells were exposed to either standard medium, PMA, EtOH or raising concentrations of compounds AF102B or NSC001 (0-2000 µM). Cell viability was detected by absorbance measurements utilizing the PrestoBlue colorimetric assay (PrestoBlue Cell Viability Reagent, A13261, Thermo Fisher, Switzerland). Cell viability was assessed directly after compound application at 0 h and after 1 h, 3 h and 24 h. Data of the individual compound concentrations is displayed after normalization to medium control at the respective time point. Compared to medium control, Ethanol administration to the cell medium reduced cell viability in a time- and concentration-dependent manner, serving as negative control (FIG. 5A). In contrary, cell viability was increased in regards to medium control by application of PMA or treatment with compounds NSC001 and AF102B (FIG. 5A,B,C). The effect of compounds NSC001 and AF102B (1-2000 µM) persisted after 24 hours of treatment while the rapid effect of PMA 1 hour after administration was reversed to baseline.

Throughout the present description and claims, terms which are defined as they are introduced retain those definitions throughout the description and claims.

The invention claimed is:

1. A method for promoting or activating microglia cells or macrophages by stimulating sTREM2 secretion in a subject in need thereof, wherein the method comprises administering to the subject a therapeutically effective amount of a compound, wherein the compound is(S)-2-ethyl-8-methyl-1-thia-4,8-diaza-spiro [4.5] decan-3-one, or a tautomer, a metabolite, a crystalline polymorph, a hydrate, or a pharmaceutically acceptable salt thereof, and wherein the subject is negative for R47H and R62H mutation in the amino acid sequence of TREM2 and has at least one functional allele of the TREM2 encoding gene.

2. The method according to claim 1, wherein the subject has no mutation in the amino acid sequence of TREM2.

3. The method according to claim 1, wherein the method comprises administering to the subject 1 mg to 100 mg of the compound.

4. The method of claim 3, wherein the method comprises administering to the subject 10 mg to 50 mg of the compound.

5. The method according to claim 1, wherein the compound is administered as an oral solution or an oral pill.

6. The method according to claim 1, wherein the subject in need thereof suffers from a neurological or neurodegenerative disease or condition, wherein said disease or condition is a tauopathy.

7. The method according to claim 1 comprising administration of a pharmaceutical composition comprising the compound and at least one pharmaceutically acceptable excipient or carrier.

8. The method of claim 7, wherein the pharmaceutical composition is a formulation of a crystalline polymorph of the compound, which is suitable for oral administration, and wherein the formulation is (i) directly compressed into tablets; or (ii) mixed with one or more excipients, and the mixture is filled in size 4, white opaque, hard gelatin, two-piece capsules to provide 5 mg or 10 mg of the compound per capsule, which can be used as an oral formulation for immediate release in the gastrointestinal tract.

9. The method of claim 8, wherein the one or more excipients are selected from pregelatinized starch, microcrystalline cellulose, colloidal silicon dioxide, and stearic acid.

10. The method of claim 1, wherein the subject in need thereof suffers from a neurological or neurodegenerative disease or condition, wherein said disease or condition is selected from the group consisting of Alzheimer's disease, frontotemporal dementia, Parkinson's disease, amyotrophic lateral sclerosis, and Nasu-Hakola disease (NHD, also known as polycystic lipomembranous osteodysplasia with sclerosing leukoencephalopathy, PLOSL).

11. The method of claim 1, wherein the subject is at the stage of predementia or prodromal Alzheimer's disease.

12. The method of claim 1, wherein the subject has characteristic pathophysiologic changes of Alzheimer's disease but no evidence of clinical impact.

13. The method of claim 1, wherein the subject has characteristic pathophysiologic changes of Alzheimer's disease and subtle detectable abnormalities on sensitive neuropsychological measures, but no functional impairment.

14. The method of claim 1, wherein the method further comprises administering to the subject an anti-inflammatory agent.

15. A method for maintaining, promoting, or activating microglia cells or macrophages by stimulating sTREM2 secretion in vitro comprising contacting a cell culture comprising microglia cells and/or macrophages with a human M1 mAChR agonist at a concentration of from about 1 µM to about 10 µM, wherein the human M1 mAChR agonist is(S)-2-ethyl-8-methyl-1-thia-4,8-diaza-spiro [4.5] decan-3-one, or a tautomer, a metabolite, a crystalline polymorph, a hydrate, or a pharmaceutically acceptable salt thereof.

* * * * *